(12) United States Patent
Haick et al.

(10) Patent No.: US 9,678,059 B2
(45) Date of Patent: Jun. 13, 2017

(54) DETECTION, STAGING AND GRADING OF BENIGN AND MALIGNANT TUMORS

(75) Inventors: Hossam Haick, Haifa (IL); Gregory Shuster, Ramat Ishay (IL)

(73) Assignee: Technion Research & Development Foundation Ltd., Haifa (IL)

( * ) Notice: Subject to any disclaimer, the term of this patent is extended or adjusted under 35 U.S.C. 154(b) by 232 days.

(21) Appl. No.: 13/697,554

(22) PCT Filed: May 22, 2011

(86) PCT No.: PCT/IL2011/000400
§ 371 (c)(1),
(2), (4) Date: Nov. 13, 2012

(87) PCT Pub. No.: WO2011/148371
PCT Pub. Date: Dec. 1, 2011

(65) Prior Publication Data
US 2013/0059758 A1  Mar. 7, 2013

Related U.S. Application Data

(60) Provisional application No. 61/347,424, filed on May 23, 2010.

(51) Int. Cl.
| | | |
|---|---|---|
| *G01N 33/497* | (2006.01) |
| *B82Y 15/00* | (2011.01) |
| *G01N 33/574* | (2006.01) |
| *G01N 33/58* | (2006.01) |

(52) U.S. Cl.
CPC ............ *G01N 33/497* (2013.01); *B82Y 15/00* (2013.01); *G01N 33/57415* (2013.01); *G01N 33/587* (2013.01); *G01N 2033/4975* (2013.01); *G01N 2800/50* (2013.01); *G01N 2800/56* (2013.01)

(58) Field of Classification Search
None
See application file for complete search history.

(56) References Cited

U.S. PATENT DOCUMENTS

| | | |
|---|---|---|
| 5,571,401 A | 11/1996 | Lewis |
| 5,698,089 A | 12/1997 | Lewis |
| 6,010,616 A | 1/2000 | Lewis |
| 6,537,498 B1 | 3/2003 | Lewis |
| 6,746,960 B2 | 6/2004 | Goodman |
| 6,773,926 B1 | 8/2004 | Freund |
| 6,890,715 B1 | 5/2005 | Lewis |
| 7,052,854 B2 | 5/2006 | Melker |
| 2005/0079551 A1 | 4/2005 | Mizuno |
| 2005/0287552 A1 | 12/2005 | Lin |
| 2007/0114138 A1 | 5/2007 | Krasteva |
| 2011/0269632 A1 | 11/2011 | Haick |

FOREIGN PATENT DOCUMENTS

| | | |
|---|---|---|
| CN | 101135689 | 3/2008 |
| EP | 1215485 | 6/2002 |
| FR | 2783051 | 3/2000 |
| WO | 99/27357 | 6/1999 |
| WO | 00/00808 | 1/2000 |
| WO | 00/14520 | 3/2000 |
| WO | 2009/066293 | 5/2009 |
| WO | 2010/064239 | 6/2010 |
| WO | 2010/079490 | 7/2010 |

OTHER PUBLICATIONS

Dragonieri et al, Lung Cancer 64, (2009) 166-170.*
Han et al, Sensors and Actuators B, 106, 2005, p. 431-441.*
Phillips et al, Lancet, 3563, p. 1930-1933, 1999.*
Natale et al, Sensors for Chemical and Biological Applications, p. 233-247, 2010.*
Boiselle et al., (2000) Lung cancer detection in the 21st century: potential contributions and challenges of emerging technologies. AJR Am J Roentgenol 175(5): 1215-21.
Chen et al., (2005) A study of an electronic nose for detection of lung cancer based on a virtual SAW gas sensors array and imaging recognition method. Meas Sci Technol 16(8): 1535-1546.
Chen et al., (2007) A study of the volatile organic compounds exhaled by lung cancer cells in vitro for breath diagnosis. Cancer 110(4): 835-44.
Di Natale et al., (2003) Lung cancer identification by the analysis of breath by means of an array of non-selective gas sensors. Biosens Bioelectron 18(10): 1209-18.
Dovgolevsky et al., (2010) Monolayer-capped cubic platinum nanoparticles for sensing nonpolar analytes in highly humid atmospheres. J Phys Chem C 114(33): 14042-14049.
Ebeler et al., (1997) Quantitative analysis by gas chromatography of volatile carbonyl compounds in expired air from mice and human. J Chromatogr B Biomed Sci Appl 702(1-2): 211-5.
Ibanez et al., (2008) Chemiresistive Sensing of Volatile Organic Compounds with Films of Surfactant-Stabilized Gold and Gold-Silver Alloy Nanoparticles. ACS Nano 2(8): 1543-1552.
Jemal et al., (2008) Cancer statistics, 2008. CA Cancer J Clin 58(2): 71-96.
Joseph et al., (2008) Gold Nanoparticle/Organic Networks as Chemiresistor Coatings: The Effect of Film Morphology on Vapor Sensitivity. J Phys Chem C 112 (32): 12507-12514.
Kuzmych et al., (2007) Carbon nanotube sensors for exhaled breath components. Nanotechnology 18 375502 (7pp).
Li et al., (2007) Inkjet printed chemical sensor array based on polythiophene conductive polymers. Sensors and Actuators B 123 (2007): 651-660.

(Continued)

*Primary Examiner* — Samuel Woolwine
*Assistant Examiner* — Valerie Toodle
(74) *Attorney, Agent, or Firm* — Roach Brown McCarthy & Gruber, P.C.; Kevin D. McCarthy

(57) ABSTRACT

The present invention provides a method for detecting and grading benign and malignant tumors using at least one sensor of conductive nanoparticles capped with an organic coating in conjunction with a learning and pattern recognition algorithm. The method utilizes a plurality of response induced parameters to obtain improved sensitivity and selectivity for diagnosis, prognosis, monitoring and staging various types of cancers, or for identifying or grading benign or malignant tumors.

18 Claims, 9 Drawing Sheets

(56) References Cited

OTHER PUBLICATIONS

Lonergan et al., (1996) Array-based vapor sensing using chemically sensitive, carbon black—polymer resistors. Chem Mater 8 (9): 2298-2312.
Machado et al., (2005) Detection of lung cancer by sensor array analyses of exhaled breath. Am J Respir Crit Care Med 171(11): 1286-91.
Mazzone (2008) Analysis of volatile organic compounds in the exhaled breath for the diagnosis of lung cancer. J Thorac Oncol 3(7): 774-80.
Mazzone (2008) Progress in the development of a diagnostic test for lung cancer through the analysis of breath volatiles. J Breath Res 2(3): 037014.
Mazzone et al., (2007) Diagnosis of lung cancer by the analysis of exhaled breath with a colorimetric sensor array. Thorax 62(7): 565-8.
Meyer and Hostetter (2007) Uremia. N Engl J Med 357(13): 1316-25.
O'Neill et al., (1988) A computerized classification technique for screening for the presence of breath biomarkers in lung cancer. Clin Chem 34(8): 1613-8.
Pang et al., (2005) Humidity effect on the monolayer-protected gold nanoparticles coated chemiresistor sensor for VOCs analysis. Talanta 65(5): 1343-8.
Paska et al., (2011) Enhanced sensing of nonpolar volatile organic compounds by silicon nanowire field effect transistors. ACS Nano 5(7): 5620-6.
Peng et al., (2008) Detecting simulated patterns of lung cancer biomarkers by random network of single-walled carbon nanotubes coated with nonpolymeric organic materials. Nano Lett 8(11): 3631-5.
Peng et al., (2009) Detection of nonpolar molecules by means of carrier scattering in random networks of carbon nanotubes: toward diagnosis of diseases via breath samples. Nano Lett 9(4): 1362-8.
Phillips et al., (1999) Volatile organic compounds in breath as markers of lung cancer: a cross-sectional study. Lancet 353(9168): 1930-3.
Raman et al., (2008) Bioinspired methodology for artificial olfaction. Anal Chem 80(22): 8364-71.
Shi et al., (2001) Uniform deposition of ultrathin polymer films on the surfaces of Al2O3 nanoparticles by a plasma treatment. Appl Phys Lett 78: 1243.
Smith et al., (2003) Quantification of acetaldehyde released by lung cancer cells in vitro using selected ion flow tube mass spectrometry. Rapid Commun Mass Spectrom 17(8): 845-50.
Steinecker et al., (2007) Model of vapor-induced resistivity changes in gold-thiolate monolayer-protected nanoparticle sensor films. Anal Chem 79(13): 4977-86.
Sun et al., (2000) Monodisperse FePt nanoparticles and ferromagnetic FePt nanocrystal superlattices. Science 287: 1989-1992.
The World Health Report 2004. Annex table 2 deaths by cause, sex and mortality stratum in WHO regions, estimates for 2002. The World Health Organization. Available at http://who.int/whr/2004/en.
Wehinger et al., (2007) Lung cancer detection by proton transfer reaction mass-spectrometric analysis of human breath gas. International Journal of Mass Spectrometry 265(1): 49-59.
Zhang et al., (2002) Vapour sensing using surface functionalized gold nanoparticles. Nanotechnology 13: 439-444.
Brust, Mathias et al., (1994) Synthesis of thiol-derivatised gold nanoparticles in a two-phase Liquid—Liquid system. J. Chem. Soc., Chem. Commun., 7:801-802.
Coelho, Leiliane et al., (2007) Breath air analysis and its use as a biomarker in biological monitoring of occupational and environmental exposure to chemical agents. J Chromatography B 853(1-2):1-9.
Cortes, Corinna and Vapnik, Vladimir (1995) Support-vector networks. Machine Learning,20(3):273-297.
Dovgolevsky, Ekaterina et al., (2008) Direct Observation of the Transition Point Between Quasi-Spherical and Cubic Nanoparticles in a Two-Step Seed-Mediated Growth Method. Small 4(11):2059-2066.
Dovgolevsky, Ekaterina et al., (2009) Chemically Sensitive Resistors Based on Monolayer-Capped Cubic Nanoparticles: Towards Configurable Nanoporous Sensors. Small 5(10):1158-1161.
Evans, Stephen D. et al., (2000) Vapour sensing using hybrid organic-inorganic nanostructured materials. J Mater Chem 10:183-188.
Hall, Mark et al., (2009) The WEKA Data Mining Software: An Update.SIGKDD Explorations 11(1):10.
Han, Li et al., (2005) Nanoparticle-structured sensing array materials and pattern recognition for VOC detection. Sensors and Actuators B: Chemical 106(1):431-441.
Hostetler, Michael J.et al., (1998) Alkanethiolate Gold Cluster Molecules with Core Diameters from 1.5 to 5.2 nm: Core and Monolayer Properties as a Function of Core Size. Langmuir 14(1):17-30.
Ouyang, Gangfeng and Pawliszyn, Janusz (2006) SPME in environmental analysis. Anal Bioanal Chem 386(4):1059-1073.
Peng, Gang et al., (2009) Diagnosing lung cancer in exhaled breath using gold nanoparticles. Nat Nanotechnol 4 (10):669-673.
Peng, Gang et al., (2010) Detection of lung, breast, colorectal, and prostate cancers from exhaled breath using a single array of nanosensors. Br J Cancer 103(4)542-551.
Phillips, Michael et al., (2003) Volatile markers of breast cancer in the breath. Breast J 9(3):184-191.
Phillips, Michael et al., (2006) Prediction of breast cancer using volatile biomarkers in the breath. Breast Cancer Res Treat 99(1):19-21.
Phillips, M. et al., (2007) Prediction of lung cancer using volatile biomarkers in breath. Cancer Biomark 3(2):95-109.
Phillips, Michael et al., (2010) Volatile biomarkers in the breath of women with breast cancer. J Breath Res 4(2):026003.
Silkoff, P. E. et al., (2005) ATS/ERS Recommendations for Standardized Procedures for the Online and Offline Measurement of Exhaled Lower Respiratory Nitric Oxide and Nasal Nitric Oxide, 2005. Am J Respir Crit Care Med 171(8):912-930.
Shuster, Gregory (2011) Classification of breast cancer precursors through exhaled breath. Breast Cancer Res Treat 126(3):791-796.
Zhao, Xiao-Mei et al., (1997) Soft lithographic methods for nanofabrication. J Mater Chem 7(7):1069-1074.
Wohltjen, Hank and Snow, Arthur W. (1998) Colloidal Metal-Insulator-Metal Ensemble Chemiresistor Sensor. Anal Chem 70(14):2856-2859.
ISR of PCT/IL2011/000400 mailed Oct. 13, 2011.
Classification of breast cancer precursors through exhaled breath, G.Shuster, Z.Gallimidi, A.Heyman Reiss, E.Dovgolevsky, S.Billan, R.Abdah-Bortnyak, A.Kuten, A.Engel, A.Shiban, U.Tisch, H.Haick, Breast Cancer Res Treat (2011) 126:791-796.
Classification of lung cancer histology by gold nanoparticle sensors, Barash O, Peled N, Tisch U, Bunn PA Jr, Hirsch FR, Haick H, Nanomedicine. Jul. 2012;8(5):580-9.
A nanomaterial-based breath test for distinguishing gastric cancer from benign gastric conditions, Z-q Xu, Y Y Broza, R Ionsecu, U Tisch, L Ding, H Liu, Q Song, Y-y Pan, F-x Xiong, K-s Gu, G-p Sun, Z-d Chen, M Leja and H Haick, British Jornal of Cancer (2013) 108,941-950.
Analysis of exhaled breath for diagnosing head and neck squamous cell carcinoma: a feasibility study, M Gruber, U Tisch, R Jeries, H Amal, M Hakim, O Ronen, T Marshak, D Zimmerman, O Israel, E Amiga, I Doweck, and H Haick, British Journal of Cancer (2014) 111,790-798.
The scent fingerprint of hepatocarcinoma: in-vitro metastasis prediction with volatile organic compounds (VOCs), H. Amal, L.Ding, B-b. Liu, U. Tisch, Z-q Xu, D-y. Shi, Y.Zhao, J.Chen, R-x.Sun, H.Liu, S-L.Ye, Z-y.Tang, H.Haick, International Journal of Nanomedicine 2012:7 4135-4146.

* cited by examiner

DETECTION, STAGING AND GRADING OF BENIGN AND MALIGNANT TUMORS

FIELD OF THE INVENTION

The present invention relates to a method for detecting benign and malignant tumors using at least one sensor of conductive nanoparticles capped with an organic coating.

BACKGROUND OF THE INVENTION

Breast cancer is the most common cancer diagnosed in the U.S. and the second leading cause of cancer related death of women. Fortunately, breast cancer mortality has been declining since the 1990s, mainly due to the introduction of mammography screening at the early 1980s. Presently, mammography is used for widespread screening aimed at early diagnosis of breast cancer. However, mammography uses X-rays for breast imaging which poses significant cumulative risks of initiating and promoting breast cancer due to radiation exposure. Moreover, since the image quality depends on the breast's structure, mammography is primarily suitable for women approaching menopause and post-menopausal women. Young women who are at risk of developing breast cancer (e.g., women with a family history of breast cancer and/or BRCA mutations) cannot obtain a conclusive diagnosis based on mammography screening alone. Another population for which mammography is less suitable is women who are undergoing treatment for breast cancer. The treatment causes irreversible changes to the structure of the breast, which often leads to obscure breast images. Thus, monitoring breast cancer using mammography is often not reliable.

Other available techniques for early diagnosis and monitoring of breast cancer include magnetic resonance imaging (MRI) and ultrasound imaging. However, it has been shown that ultrasound cannot identify breast tumors unambiguously. In addition, although the sensitivity of MRI to breast tumors is high, its specificity to breast tumors is significantly lower in comparison to that of mammography. This leads to false positive results causing anxiety to patients and subjecting healthy women to unnecessary biopsies and other invasive follow-up tests.

Breath analysis has long been recognized as a reliable technique for diagnosing certain medical conditions through the detection of volatile organic compounds (VOCs). The composition of VOCs in exhaled breath is dependent upon cellular metabolic processes and it includes, inter alia, saturated and unsaturated hydrocarbons, oxygen containing compounds, sulfur containing compounds, and nitrogen containing compounds.

In exhaled breath of patients with cancer, elevated levels of certain VOCs including, volatile $C_4$-$C_{20}$ alkane compounds, specific monomethylated alkanes as well as benzene derivatives were found (Phillips et al., Cancer Biomark., 3(2), 2007, 95). The breath methylated alkane contour (BMAC) demonstrated differences between healthy volunteers and women with an abnormal mammogram whose biopsies were negative for breast cancer (Phillips et al., The Breast Journal, 9(3), 2003, 184). Since the composition of VOCs in exhaled breath of women with breast tumors differs from that of healthy women, measuring the VOC composition of breath samples can be used to diagnose cancer. Phillips et al. (Breast Cancer Research and Treatment, 99, 2006, 19) reported the use of five VOCs, namely 2-propanol, 2,3-dihydro-1-phenyl-4(1H)-quinazolinone, 1-phenyl-ethanone, heptanal, and isopropyl myristate for predicting breast cancer using a fuzzy logic model. Recently, a combination of specific volatile biomarkers in breath samples and a multivariate algorithm were used to identify women with breast cancer (Phillips et al., J. Breath Res., 4, 2010, 026003).

Gas-sensing devices for the detection of VOCs in breath samples of cancer patients have recently been applied. Such devices perform odor detection through the use of an array of cross-reactive sensors in conjunction with pattern recognition algorithms. The array of cross-reactive sensors produces a unique response pattern upon exposure to VOCs, said pattern is then analyzed using pattern recognition algorithms in order to glean information on the identity of the different VOCs and their composition.

Films composed of nanoparticles capped with an organic coating ("NPCOCs") as gas-sensing devices are disclosed in e.g. U.S. Pat. Nos. 5,571,401, 5,698,089, 6,010,616, 6,537,498, 6,746,960, 6,773,926; Patent Application Nos. WO 00/00808, FR 2,783,051, US 2007/0114138; and in Wohltjen et al. (Anal. Chem., 70, 1998, 2856), and Evans et al. (J. Mater. Chem., 8, 2000, 183).

U.S. Pat. No. 7,052,854 discloses systems and methods for ex-vivo diagnostic analysis using nanostructure-based assemblies comprising a nanoparticle, a means for detecting a target analyte/biomarker, and a surrogate marker. The sensor technology is based on the detection of the surrogate marker which indicates the presence of the target analyte/biomarker in a sample of a bodily fluid.

EP 1,215,485 discloses chemical sensors comprising a nanoparticle film formed on a substrate, the nanoparticle film comprising a nanoparticle network interlinked through linker molecules having at least two linker units. The linker units are capable of binding to the surface of the nanoparticles and at least one selectivity-enhancing unit having a binding site for reversibly binding an analyte molecule. A change of a physical property of the nanoparticle film is detected through a detection means.

WO 2009/066293 to one of the inventors of the present invention discloses a sensing apparatus for detecting volatile and non-volatile compounds. The apparatus comprises sensors of cubic nanoparticles capped with an organic coating. Further disclosed are methods of use thereof in detecting certain biomarkers for diagnosing various diseases and disorders including cancer.

WO 2010/079490 to one of the inventors of the present invention discloses a sensor array comprising conductive nanoparticles characterized by a narrow particle size distribution capped with an organic coating of varying thickness for detecting VOCs indicative of various types of cancer.

There is an unmet need for the unambiguous distinction between malignant tumors and benign tumors, using non-invasive techniques. There further remains a need for a fast responsive sensor array which provides sensitivity as well as selectivity for specific VOCs indicative of benign or malignant tumors for diagnosis, prognosis and monitoring various types of cancer.

SUMMARY OF THE INVENTION

The present invention provides a method of diagnosing, monitoring, prognosing or staging various types of cancer, or identifying or grading a benign or malignant tumor, using at least one sensor comprising conductive nanoparticles capped with an organic coating and a pattern recognition algorithm. Instead of relying merely on direct measurement of the response detected by the sensor(s), the present invention discloses a plurality of response induced parameters from each sensor thereby enabling the derivation of unambiguous determination from a small number of sensors. Thus, the method utilizes a plurality of response induced parameters from a single sensor or from a plurality of sensors to provide a composite picture regarding the presence, absence or staging of the cancer, and/or the nature and grade of the tumor (i.e., benign, pre-malignant or malignant). The present invention further provides a sensor array comprising five sensors of spherical gold nanoparticles capped with various organic coatings and one sensor of cubic platinum nanoparticles capped with benzylmercaptan for detecting volatile organic compounds (VOCs) indicative of benign and malignant breast tumors. The sensor array may be used in conjunction with a learning and pattern recognition analyzer. The method and sensor array of the present invention provide improved sensitivity and selectivity for diagnosis, prognosis and monitoring of various types of cancer and for determining the stages and grades of tumors, and thus offer significant advantages over the prior art.

The present invention discloses the measurement of a plurality of response induced parameters from at least one sensor upon exposure to a test sample comprising measuring a response and extracting a plurality of response induced parameters from the measured response.

The invention is based in part on the unexpected finding that the measurement of a plurality of response induced parameters from a sensor or a plurality of sensors upon exposure to a test sample provides improved selectivity in detecting VOC biomarkers. The plurality of response induced parameters enables the diagnosis of various types of cancer and their staging, as well as a distinction between malignant tumors and benign tumors and further provides information regarding the grade of the tumors. Additionally, disclosed herein for the first time is a sensor array comprising six sensors of conductive nanoparticles capped with organic coatings which provides enhanced sensitivity and selectivity for VOCs indicative of benign and malignant breast tumors. The use of the sensor array in conjunction with a learning and pattern recognition algorithm provides the grading of breast tumors or staging of breast cancer.

According to one aspect, the present invention provides a method of diagnosing, monitoring, prognosing or staging cancer or identifying or grading a benign or malignant tumor in a subject, the method comprising the steps of: (a) providing a system comprising (i) at least one sensor comprising conductive nanoparticles capped with an organic coating, and (ii) a learning and pattern recognition analyzer wherein the learning and pattern recognition analyzer receives sensor signal outputs and compares them to stored data, (b) exposing the at least one sensor to a test sample selected from exhaled breath and at least one bodily fluid or secretion of the subject, (c) measuring a plurality of response induced parameters from the at least one sensor upon exposure to the test sample, said response induced parameters generate a plurality of response patterns, and (d) using a learning and pattern recognition algorithm to analyze the response patterns by comparing them to stored data obtained from a control sample whereby significantly different response patterns of the test sample as compared the control sample is indicative of cancer or a malignant or benign tumor, as well as their stage or grade.

In certain embodiments, the method disclosed herein further provides the differentiation between healthy subjects, subjects having a malignant tumor, subjects having a benign tumor, subjects having different stages of cancer and subjects having different grades of a benign or malignant tumor.

In various embodiments, the cancer is selected from breast, brain, ovarian, colon, prostate, kidney, bladder, oral, and skin cancers. Each possibility represents a separate embodiment of the invention.

In other embodiments, the benign or malignant tumor is selected from breast, brain, ovarian, colon, prostate, kidney, bladder, oral, and skin tumors. Each possibility represents a separate embodiment of the invention.

In an exemplary embodiment, the method of the present invention is designated to monitoring, prognosing or staging breast cancer or identifying or grading a benign or malignant breast tumor in a subject. Typically, the subject is a woman.

In various embodiments, the system comprises a single sensor comprising conductive nanoparticles capped with an organic coating. In other embodiments, the system comprises a sensor array comprising a plurality of sensors comprising between 2 and 100 sensors, more preferably between 2 and 50 sensors and most preferably between 2 and 25 sensors. In one particular example, the sensor array comprises 6 sensors.

In some embodiments, the conductive nanoparticles are metals and metal alloys selected from the group consisting of Au, Ag, Ni, Co. Pt, Pd, Cu, Al, Au/Ag, Au/Cu, Au/Ag/Cu, Au/Pt, Au/Pd, Au/Ag/Cu/Pd, Pt/Rh, Ni/Co, and Pt/Ni/Fe. Each possibility represents a separate embodiment of the invention. In one embodiment, the conductive nanoparticles are Au nanoparticles. In another embodiment, the conductive nanoparticles are Pt nanoparticles. In yet another embodiment, the conductive nanoparticles comprise metals and metal alloys selected from Au and Pt nanoparticles and combinations thereof.

In certain embodiments, the system comprises a sensor array comprising a plurality of sensors comprising Au nanoparticles capped with an organic coating and at least one sensor comprising Pt nanoparticles capped with an organic coating. In specific embodiments, the ratio of sensors comprising Au nanoparticles and sensors comprising Pt nanoparticles in the sensor array is from 1:1 to 10:1. In other embodiments, the ratio of sensors comprising Au nanoparticles and sensors comprising Pt nanoparticles in the sensor array is from 3:1 to 7:1. In exemplary embodiments, the ratio of sensors comprising Au nanoparticles and sensors comprising Pt nanoparticles in the sensor array is 5:1.

In other embodiments, the conductive nanoparticles are metals and metal alloys having a morphology selected from cubic, spherical, and spheroidal. Each possibility represents a separate embodiment of the invention.

In various embodiments, the coating of the conductive nanoparticles comprises a monolayer or multilayers of organic compounds, wherein the organic compounds can be small molecules, monomers, oligomers or polymers such as short polymeric chains. In particular embodiments, the organic compounds are selected from the group consisting of alkylthiols, arylthiols, alkylarylthiols, alkylthiolates, ω-functionalized alkylthiolates, arenethiolates, (γ-mercaptopropyl)-methyloxysilane, dialkyl sulfides, diaryl sulfides, alkylaryl sulfides, dialkyl disulfides, diaryl disulfides, alkylaryl disulfides, alkyl sulfites, aryl sulfites, alkylaryl sulfites, alkyl sulfates, aryl sulfates, alkylaryl sulfates, calixarenes, xanthates, oligonucleotides, polynucleotides, dithiocarbamate, alkyl amines, aryl amines, diaryl amines, dialkyl amines, alkylaryl amines, arene amines, alkyl phosphines, aryl phosphines, dialkyl phosphines, diaryl phosphines, alkylaryl phosphines, phosphine oxides, alkyl carboxylates, aryl carboxylates, dialkyl carboxylates, diaryl carboxylates, alkylaryl carboxylates, cyanates, isocyanates, peptides, proteins, enzymes, polysaccharides, phospholipids, and combinations and derivatives thereof. Each possibility represents a separate embodiment of the invention.

In some embodiments, the organic coating is selected from the group consisting of alkylthiols with $C_3$-$C_{24}$ chains, ω-functionalized alkanethiolates, arenethiolate, (γ-mercaptopropyl)tri-methyloxysilane, dialkyl disulfides, calixarenes, xanthates, oligonucleotides, polynucleotides, peptides, proteins, enzymes, polysaccharides, phospholipids, and combinations thereof. Each possibility represents a separate embodiment of the invention.

In a particular embodiment, the organic coating comprises alkylthiols with $C_3$-$C_{24}$ chains. In another embodiment, the organic coating comprises octadecylamine. In yet another embodiment, the organic coating is selected from alkanethiolates, arenethiolates and calixarenes. Each possibility represents a separate embodiment of the invention.

In an exemplary embodiment, the organic coating is selected from the group consisting of tert-dodecanethiol, 2-ethylhexanethiol, 2-mercaptobenzyl alcohol, 2-mercaptobenzoazole, calixarene, benzylmercaptan and combinations thereof. Each possibility represents a separate embodiment of the invention.

In other embodiments, the sensors of conductive nanoparticles capped with an organic coating are in a configuration selected from the group consisting of 1D wires, 2D films, and 3D assemblies. Each possibility represents a separate embodiment of the invention.

In specific embodiments, the sensors of conductive nanoparticles capped with an organic coating can be used in a configuration selected from the group consisting of a chemiresistor, a chemicapacitor, a Field Effect Transistor (FET) and combinations thereof. Each possibility represents a separate embodiment of the invention.

In certain embodiments, the method of the present invention utilizes bodily fluids or secretions selected from the group consisting of serum, urine, feces, sweat, vaginal discharge, saliva and sperm. Each possibility represents a separate embodiment of the invention.

In specific embodiments, the method of the present invention is applicable for detecting VOCs in exhaled breath samples. In exemplary embodiments, the method of the present invention further comprises the step of increasing VOC concentrations using an apparatus for collecting breath samples. In specific embodiments, the apparatus is designed to collect alveolar breath. In other embodiments, the apparatus comprises at least one of a breath concentrator and a dehumidifying unit.

In particular embodiments, the method of the present invention further comprises the use of at least one of a chemiresistor, a chemicapacitor, a quartz crystal microbalance (QCM), a bulk acoustic wave (BAW) and a surface acoustic wave (SAW) resonator, an electrochemical cell, a surface plasmon resonance (SPR), and an optical spectroscope. Each possibility represents a separate embodiment of the invention.

In various embodiments, the learning and pattern recognition analyzer utilizes an algorithm selected from artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical algorithms including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the invention. In an exemplary embodiment, the algorithm utilized by the learning and pattern recognition analyzer is principle component analysis (PCA). In another exemplary embodiment, the algorithm utilized by the learning and pattern recognition analyzer is support vector machine (SVM).

In specific embodiments, the step of measuring a plurality of response induced parameters from the at least one sensor upon exposure to the test sample comprises measuring a response and extracting a plurality of response induced parameters from the measured response.

In certain embodiments, the measured response comprises a change in any one or more of an electrical property such as, but not limited to, conductivity, resistance, impedance, capacitance, inductance, or optical properties of the sensor(s) upon exposure to VOC(s) to be detected. Each possibility represents a separate embodiment of the invention.

In particular embodiments, the response induced parameters are selected from the group consisting of steady state normalized response, the time interval for obtaining steady state normalized response, and the time required to reach baseline after removal of the test sample. Each possibility represents a separate embodiment of the invention.

In exemplary embodiments, the response induced parameters are selected from the group consisting of full non steady state response at the beginning of the signal, full non steady state response at the beginning of the signal normalized to baseline, full non steady state response at the middle of the signal, full non steady state response at the middle of the signal normalized to baseline, full steady state response, full steady state response normalized to baseline, area under non steady state response, area under steady state response, the gradient of the response upon exposure to the test sample, the gradient of the response upon removal of the test sample, the time required to reach a certain percentage of the response, such as the time required to reach 10%, 20%, 30%, 40%, 50%, 60%, 70%, 80%, 90% or 100% of the response upon exposure to the test sample, and the time required to reach a certain percentage of the response, such as the time required to reach 100%, 90%, 80%, 70%, 60%, 50%, 40%, 30%, 20% or 10% of the response upon removal of the test sample. Each possibility represents a separate embodiment of the invention.

In alternative embodiments, the step of measuring a plurality of response induced parameters from the at least one sensor upon exposure to the test sample comprises measuring a response and fitting the response to a function or a plurality of functions whereby the response induced parameters are selected from function constants, function coefficients and a combination thereof. Each possibility represents a separate embodiment of the invention.

According to another aspect, the present invention provides a sensor array for detecting VOCs indicative of breast cancer or a benign or malignant breast tumor, said sensor array comprises five sensors wherein each of the five sensors comprises gold nanoparticles capped with an organic coating selected from tert-dodecanethiol, 2-ethylhexanethiol, 2-mercaptobenzyl alcohol, 2-mercaptobenzoazole and calixarene, and one sensor of platinum nanoparticles capped with benzylmercaptan.

In one embodiment, the present invention provides a system for detecting a pattern of VOCs indicative of breast cancer or a benign or malignant breast tumor, said system comprises (i) a sensor array comprising five sensors wherein each of the five sensors comprises Au nanoparticles capped with an organic coating selected from tert-dodecanethiol, 2-ethylhexanethiol, 2-mercaptobenzyl alcohol, 2-mercaptobenzoazole and calixarene, and one sensor of Pt nanoparticles capped with benzylmercaptan, and (ii) a learning and pattern recognition analyzer wherein the learning and pattern recognition analyzer receives sensor signal outputs and compares them to stored data.

In another embodiment, the present invention provides a method of diagnosing, monitoring, prognosing or staging cancer or identifying or grading a benign or malignant tumor in a subject using the sensor array and system of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
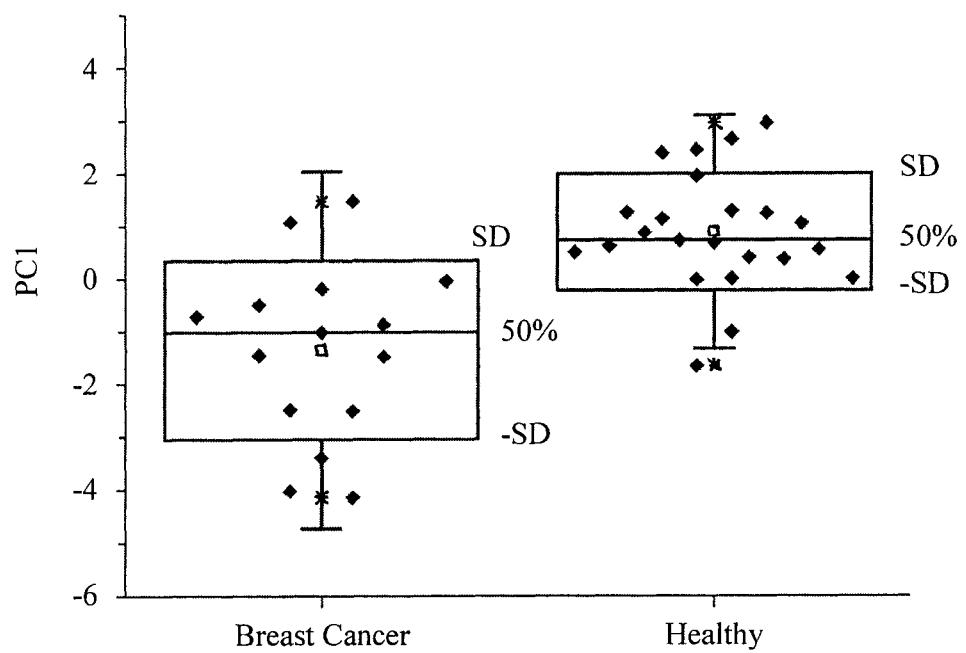
FIG. 1. Separation to healthy and BC populations using a single sensor and four response induced parameters.

The present invention provides a method of diagnosing, monitoring, prognosing or staging cancer, preferably breast cancer using at least one sensor comprising conductive nanoparticles capped with an organic coating and a learning and pattern recognition analyzer. The invention further provides a method of distinguishing between malignant and benign tumors, and a method of grading tumors by measuring a response and extracting a plurality of response induced parameters from said response.

The method, according to the principles of the present invention is designed for detecting volatile organic compounds (VOCs) indicative of benign or malignant tumors using a system comprising at least one sensor and a learning and pattern recognition algorithm. Upon adsorption of a VOC, the film/assembly of conductive nanoparticles capped with an organic coating (NPCOCs) can either swell, or aggregate. In thin films of NPCOCs a relative change in the permittivity constant of the film upon VOC adsorption may be generated. The response introduced upon VOC exposure is determined by the nature of the interaction between analyte species and the molecular coating of the nanoparticles. It is now disclosed for the first time that measuring a plurality of response induced parameters upon VOC exposure of the sensor(s) generates a plurality of patterns which provide improved sensitivity and specificity of the analysis. This obviates the need for additional sensors and improves the discrimination between subjects with benign tumors and subjects with malignant tumors.

The present invention provides an ex-vivo method of diagnosing, monitoring, prognosing or staging cancer or alternatively identifying or grading a benign or malignant tumor in a subject. The method involves the use of a system comprising a single sensor or a sensor array comprising a plurality of sensors, wherein each sensor comprises conductive nanoparticles capped with an organic coating and a learning and pattern recognition analyzer. The system is exposed to a breath sample or a sample of bodily fluids or secretions that was obtained from a subject. Upon exposure, a response or a plurality of responses is measured using a detection means and a plurality of response induced parameters are extracted to provide an output signal comprising multiple patterns. The patterns are then analyzed by comparing them to a control pattern from a healthy subject or a subject who is afflicted with cancer using a learning and pattern recognition algorithm, whereby significantly different patterns of the test sample in comparison to the control pattern is indicative of the presence of malignant tumors or cancer, or the lack of malignancies, or the presence of benign tumors. The comparison can further provide information regarding the stage or grade of the cancer. The present invention represents a significant improvement over the prior art, in that a plurality of response induced parameters generated from a sensor or a plurality of sensors is used to provide a composite picture indicative not only of the presence or absence of cancer, but also of the different stages of the cancer or pre-cancer or even of the presence of benign tumors. This is not taught or suggested in the prior art.

According to the principles of the present invention, various types of malignant tumors/cancers can be diagnosed using the method of the present invention. The term "cancer" refers to a disorder in which a population of cells has become, in varying degrees, unresponsive to the control mechanisms that normally govern proliferation and differentiation. Cancer refers to various types of pre-malignant and malignant neoplasms and tumors, including primary tumors, and tumor metastasis. Non-limiting examples of cancers which can be diagnosed by the method of the present invention are breast, brain, ovarian, colon, prostate, kidney, bladder, oral, and skin cancers. Each possibility represents a separate embodiment of the invention. Specific examples of cancers include carcinomas, sarcomas, myelomas, leukemias, lymphomas and mixed type tumors. Particular categories of cancers include lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. Particular types of tumors include hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, and non-Hodgkin's lymphoma. Each possibility represents a separate embodiment of the invention.

The term "staging" as used herein refers to the level of spreading of the cancer disease. Common parameters which are considered when determining the stage of cancer include, but are not limited to, the size of the tumor, the penetration depth of the tumor, metastasis to adjacent organs, and metastasis to remote organs. The term "grading" as used herein refers to the level of progress of tumors and other neoplasms. In general, grading is determined using an optical microscope and it relates to the level of abnormality of the cells. A common parameter which is considered when determining the grade of a tumor includes, but is not limited to, the rate of growth and spreading of the tumor.

Within the scope of the present invention is the diagnosis, prognosis, monitoring staging and grading of breast cancer and the discrimination between breath or secretion samples of subjects having a malignant breast tumor and subjects having a benign breast tumor.

The term "malignant breast tumors" as used herein refers to carcinoma in situ and invasive cancer. Carcinoma in situ is proliferation of cancer cells within ducts or lobules and without invasion of stromal tissue. Usually, ductal carcinoma in situ (DCIS) is localized to one area but it may become invasive. Invasive carcinoma is primarily adenocarcinoma. About 80% is the infiltrating ductal type; most of the remainder is infiltrating lobular. Rare forms include medullary, mucinous, and tubular carcinomas. Paget's disease of the nipple is a form of ductal carcinoma in situ that extends into the overlying skin of the nipple and areola, manifesting with an inflammatory skin lesion. Characteristic malignant cells called Paget cells are present in the epidermis. The cancer may become invasive.

The term "pre-malignant breast tumors" as used herein refers to tumors that might become malignant, but at the time of examination, would not be classified as malignant by conventional methods. A pre-malignant breast tumor includes, for example, lobular carcinoma in situ (LCIS) which is a nonpalpable lesion which is often multifocal and bilateral. It is not malignant, but its presence indicates increased risk of subsequent invasive carcinoma in either breast.

The term "benign breast tumors" as used herein refers to fibrocystic changes and fibroadenomas. Fibrotic changes (previously, fibrocystic disease) is a catchall term that refers to mastalgia, breast cysts (e.g. galactocele), and nondescript lumpiness, which may occur in isolation or together. The fibrocystic changes may occur due to adenosis, ductal ectasia, simple fibroadenoma, fibrosis, mastitis (breast infections), mild hyperplasia, cysts, and apocrine or squamous metaplasia. Fibroadenomas are typically painless lumps which usually develop in young adolescent women.

The method of the present invention utilizes a system comprising at least one sensor, wherein the at least one sensor comprises conductive nanoparticles capped with an organic coating. The conductive nanoparticles comprise metal or metal alloys including, but not limited to, Au, Ag, Ni, Co, Pt, Pd, Cu, Al Au/Ag, Au/Cu, Au/Ag/Cu, Au/Pt, Au/Pd, Au/Ag/Cu/Pd, Pt/Rh, Ni/Co, and Pt/Ni/Fe nanoparticles. Each possibility represents a separate embodiment of the invention. In specific embodiments, the system of the present invention comprises a sensor array comprising a plurality of sensors of Au nanoparticles capped with an organic coating and at least one sensor of Pt nanoparticles capped with an organic coating. The ratio between the sensors comprising Au nanoparticles and the sensors comprising Pt nanoparticles may be optimized according to the nature of VOC(s) to be detected and may vary for example between 1:1 and 10:1, and between 3:1 and 7:1. The ratio may further be dependent on the number of sensors in the sensor array which may vary between 2 and 100, between 2 and 50, or between 2 and 25 sensors in an array. In one specific example, the sensor array comprises 6 sensors wherein the ratio between the sensors comprising Au nanoparticles and the sensors comprising Pt nanoparticles is 5:1.

The metal nanoparticles may have any desirable morphology including a cubic, a spherical or a spheroidal shape. Each possibility represents a separate embodiment of the invention.

The coating of the conductive nanoparticles comprises a monolayer or multilayers of organic compounds, wherein the organic compounds can be small molecules, monomers, oligomers or polymers (such as short polymeric chains). In particular embodiments, the organic compounds are selected from the group consisting of alkylthiols, e.g., alkylthiols with $C_3$-$C_{24}$ chains, arylthiols, alkylarylthiols, alkylthiolates, ω-functionalized alkylthiolates, arenethiolates, (γ-mercaptopropyl)tri-methyloxysilane, dialkyl sulfides, diaryl sulfides, alkylaryl sulfides, dialkyl disulfides, diaryl disulfides, alkylaryl disulfides, alkyl sulfites, aryl sulfites, alkylaryl sulfites, alkyl sulfates, aryl sulfates, alkylaryl sulfates, calixarenes, xanthates, oligonucleotides, polynucleotides, dithiocarbamate, alkyl amines, aryl amines, diaryl amines, dialkyl amines, alkylaryl amines, arene amines, alkyl phosphines, dialkyl phosphines, aryl phosphines, diaryl phosphines, alkylaryl phosphines, dialkyl phosphines, diaryl phosphines, alkylaryl phosphines, phosphine oxides, alkyl carboxylates, aryl carboxylates, dialkyl carboxylates, diaryl carboxylates, alkylaryl carboxylates, dialkyl carboxylates, diaryl carboxylates, alkylaryl carboxylates, cyanates, isocyanates, peptides, proteins, enzymes, polysaccharides, phospholipids, and combinations and derivatives thereof. Each possibility represents a separate embodiment of the invention.

Other organic compounds suitable as capping agents include, but are not limited to, alkenyl thiols, alkynyl thiols, cycloalkyl thiols, heterocyclyl thiols, heteroaryl thiols, alkenyl thiolates, alkynyl thiolates, cycloalkyl thiolates, heterocyclyl thiolates, heteroaryl thiolates, alkenyl sulfides, alkynyl sulfides, cycloalkyl sulfides, heterocyclyl sulfides, heteroaryl sulfides, alkenyl disulfides, alkynyl disulfides, cycloalkyl disulfides, heterocyclyl disulfides, heteroaryl disulfides, alkenyl sulfites, alkynyl sulfites, cycloalkyl sulfites, heterocyclyl sulfites, heteroaryl sulfites, alkenyl sulfates, alkynyl sulfates, cycloalkyl sulfates, heterocyclyl sulfates, heteroaryl sulfates, alkenyl amines, alkynyl amines, cycloalkyl amines, heterocyclyl amines, heteroaryl amines, alkenyl carboxylates, alkynyl carboxylates, cycloalkyl carboxylates, heterocyclyl carboxylates, and heteroaryl carboxylates. Each possibility represents a separate embodiment of the invention.

In exemplary embodiments, the organic coating is selected from alkanethiolates, arenethiolates and calixarenes. Each possibility represents a separate embodiment of the invention. In other embodiments, the organic coating is selected from the group consisting of tert-dodecanethiol, 2-ethylhexanethiol, 2-mercaptobenzyl alcohol, 2-mercaptobenzoazole, calixarene, benzylmercaptan, and combinations thereof. Each possibility represents a separate embodiment of the invention. In one embodiment, the organic coating comprises octadecylamine.

An "alkyl" group refers to a saturated aliphatic hydrocarbon, including straight-chain, branched-chain and cyclic alkyl groups. In one embodiment, the alkyl group has 1-12 carbons designated here as $C_1$-$C_{12}$-alkyl. In another embodiment, the alkyl group has 2-6 carbons designated here as $C_2$-$C_6$-alkyl. In another embodiment, the alkyl group has 2-4 carbons designated here as $C_2$-$C_4$-alkyl. In an exemplary embodiment, the alkyl group has 3-24 carbons designated here as $C_3$-$C_{24}$ alkyl. The alkyl group may be unsubstituted or substituted by one or more groups selected from halogen, haloalkyl, acyl, amido, ester, cyano, nitro, and azido. Each possibility represents a separate embodiment of the invention.

A "cycloalkyl" group refers to a non-aromatic mono- or multicyclic ring system. In one embodiment, the cycloalkyl group has 3-10 carbon atoms. In another embodiment, the cycloalkyl group has 5-10 carbon atoms. Exemplary monocyclic cycloalkyl groups include cyclopentyl, cyclohexyl, cycloheptyl and the like. An alkylcycloalkyl is an alkyl group as defined herein bonded to a cycloalkyl group as defined herein. The cycloalkyl group can be unsubstituted or substituted with any one or more of the substituents defined above for alkyl.

An "alkenyl" group refers to an aliphatic hydrocarbon group containing at least one carbon-carbon double bond including straight-chain, branched-chain and cyclic alkenyl groups. In one embodiment, the alkenyl group has 2-8 carbon atoms (a $C_{2-8}$ alkenyl). In another embodiment, the alkenyl group has 2-4 carbon atoms in the chain (a $C_{2-4}$ alkenyl). Exemplary alkenyl groups include, but are not limited to, ethenyl, propenyl, n-butenyl, i-butenyl, 3-methylbut-2-enyl, n-pentenyl, heptenyl, octenyl, cyclohexylbutenyl and decenyl. An alkylalkenyl is an alkyl group as defined herein bonded to an alkenyl group as defined herein. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. In one embodiment, the alkynyl group has 2-8 carbon atoms in the chain (a $C_{2-8}$ alkynyl). In another embodiment, the alkynyl group has 2-4 carbon atoms in the chain (a $C_{2-4}$ alkynyl). Exemplary alkynyl groups include, but are not limited to, ethynyl, propynyl, n-butynyl, 2-butynyl, 3-methylbutynyl, n-pentynyl, heptynyl, octynyl and decynyl. An alkylalkynyl is an alkyl group as defined herein bonded to an alkynyl group as defined herein. The alkynyl group can be unsubstituted or substituted through available carbon atoms with one or more groups defined hereinabove for alkyl.

An "aryl" group refers to an aromatic monocyclic or multicyclic ring system. In one embodiment, the aryl group has 6-10 carbon atoms. The aryl is optionally substituted with at least one "ring system substituents" and combinations thereof as defined herein. Exemplary aryl groups include, but are not limited to, phenyl or naphthyl. The aryl group can also be bicyclic such as naphthyl, tricyclic and the like. An alkylaryl is an alkyl group as defined herein bonded to an aryl group as defined herein. The aryl group can be unsubstituted or substituted through available carbon atoms with one or more groups defined hereinabove for alkyl.

A "heteroaryl" group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheteroaromatic rings. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

A "heterocyclic ring" or "heterocyclyl" group refers to a five-membered to eight-membered rings that have 1 to 4 heteroatoms, such as oxygen, sulfur and/or in particular nitrogen. These five-membered to eight-membered rings can be saturated, fully unsaturated or partially unsaturated, with fully saturated rings being preferred. Exemplary heterocyclic rings include, but are not limited to, piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. An alkylheterocyclyl is an alkyl group as defined herein bonded to a heterocyclyl group as defined herein. The heterocyclyl group can be unsubstituted or substituted through available atoms with one or more groups defined hereinabove for alkyl.

"Ring system substituents" refer to substituents attached to aromatic or non-aromatic ring systems including, but not limited to, H, halo, haloalkyl, ($C_1$-$C_8$)alkyl, ($C_2$-$C_8$)alkenyl, ($C_2$-$C_8$)alkynyl, ($C_6$-$C_{10}$)aryl, acyl, amido, ester, cyano, nitro, azido, and the like.

A "halogen" or "halo" group as used herein alone or as part of another group refers to chlorine, bromine, fluorine, and iodine. The term "haloalkyl" refers to an alkyl group having some or all of the hydrogens independently replaced by a halogen group including, but not limited to, trichloromethyl, tribromomethyl, trifluoromethyl, triiodomethyl, difluoromethyl, chlorodifluoromethyl, pentafluoroethyl, 1,1-difluoroethyl bromomethyl, chloromethyl, fluoromethyl, iodomethyl, and the like.

An "acyl" group as used herein encompasses groups such as, but not limited to, formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Currently preferred acyl groups are acetyl and benzoyl.

An "alkoxy" group refers to an —O-alkyl group wherein R is alkyl as defined above.

A "thio" group as used herein alone or as part of another group refers to an SH group. The terms "alkylthio", "arylthio" or "arylalkylthio" as used herein alone or as part of another group refer to any of the above alkyl, arylalkyl or aryl groups linked to a sulfur atom.

The terms "oligonucleotide" or "polynucleotide" as used herein refer to DNA or RNA of genomic or synthetic origin, which may be single- or double-stranded, and represent the sense or antisense strand.

The terms "peptide" and "protein" as used herein refer to a polymer of amino acid residues. The terms apply to amino acid polymers in which one or more amino acid residues is an artificial chemical analogue of a corresponding naturally occurring amino acid, as well as to naturally occurring amino acid polymers.

The term "calixarenes" as used herein refers to cyclic oligomers based on a hydroxyalkylation product of a phenol and an aldehyde. Exemplary calixarenes include, but are not limited to, calix[4]arene, calix[4]arene with para-tert-butyl substituents, calix[6]arene, calix[6]arene with para-tert-butyl substituents and the like. Many more molecules that satisfy the definition of "organic coating" may be used in the same context.

According to certain embodiments, the sensor of the present invention is manufactured through a self-assembly process to produce films comprising nanoparticles capped with an organic coating (NPCOCs). The term "self-assembly" as used herein refers to a process of organization of molecules without intervening from an outside source. The self-assembly process takes place in a solution/solvent or directly on the solid-state substrate. The term "film", as used herein, corresponds to a configuration of well-arranged assembly of NPCOCs, preferably in body centered cubic (BCC) or face centered cubic (FCC) configuration.

The synthesis of NPCOCs can be produced by methods known in the art. For instance, gold nanoparticles can be synthesized using the two-phase method (Brust et al., *J. Chem. Soc. Chem. Commun.*, 801, 1994, 2) with some modifications (Hostetler et al., *Langmuir*, 14 1998, 24). Briefly, $AuCl_4^-$ is transferred from aqueous $HAuCl_4 \cdot xH_2O$ solution to a toluene solution by the phase-transfer reagent TOAB. After isolating the organic phase, excess thiols are added to the solution. The mole ratio of thiol:$HAuCl_4 \cdot xH_2O$ can vary between 1:1 and 10:1, depending on the thiol used. This is performed in order to prepare mono-disperse solution of gold nanoparticles in average size of about 5 nm. Exemplary procedures include, but are not limited to, thiol:Au mole ratios of 10:1 and 1:1 for dodecanethiol and butanethiol-capped gold nanoparticles, respectively at an average size of 5 nm. After vigorous stirring of the solution, aqueous solution of reducing agent $NaBH_4$ in large excess is added. The reaction is constantly stirred at room temperature for at least 3 hours to produce a dark brown solution of the thiol-capped Au nanoparticles. The resulting solution is further subjected to solvent removal in a rotary evaporator followed by multiple washings using ethanol and toluene.

Gold nanoparticles capped with 2-mercaptobenzoazole can be synthesized by ligand—exchange method from pre-prepared hexanethiol-capped gold nanoparticles. In a typical reaction, excess of thiol, 2-mercaptobenzoazole, is added to a solution of hexanethiol-capped gold nanoparticles in toluene. The solution is kept under constant stirring for few days in order to allow as much ligand conversion as possible. The nanoparticles are purified from free thiol ligands by repeated extractions.

Without being bound by any theory or mechanism of action, it is contemplated that sensing occurs via aggregation or swelling of the conductive nanoparticles capped with an organic coating assemblies, through various chemical interactions. The interactions include, but are not limited to, hydrogen-bonding, π-π, host-guest, van der Waals, electrostatic, charge-transfer, antigen-antibody interactions, and combinations thereof. Changes in permittivity usually occur in thin films having regions of discontinuities in chemiresistors, chemicapacitors and electrochemical cells which are composed of 2D or 3D films of metallic nanoparticles.

Exemplary methods for obtaining well-ordered two or three dimensional assemblies of NPCOCs include, but are not limited to, i. Random deposition from solution of NPCOCs on solid surfaces. The deposition is performed by drop casting, spin coating, spray coating, layer by layer deposition with or without interlinking ligands, and other similar techniques.

ii. Field-enhanced or molecular-interaction-induced deposition from solution of NPCOCs on solid surfaces.

iii. Langmuir-Blodgett or Langmuir-Schaefer techniques. The substrate is vertically plunged through self-organized/well-ordered 2D monolayer of NPCOCs at the air-subphase interface, wherein the latter being subsequently transferred onto it. Multiple plunging of the substrate through the 2D monolayer of NPCOCs at the air-subphase interface, results in the fabrication of the 3D-ordered multilayers of NPCOCs.

iv. Soft lithographic techniques, such as micro-contact printing (mCP), replica molding, micro-molding in capillaries (MIMIC), and micro-transfer molding (mTM). These methods are based on variations of self-assembly and replica molding of organic molecules and polymeric materials, for fabricating NPCOCs from nanometer-scale to a mesoscopic scale (Whitesides et al., *J. Mater. Chem.* 7, 1069, 1997).

v. Various combinations of Langmuir-Blodgett or Langmuir-Schaefer methods with soft lithographic techniques can be used to produce patterned Langmuir-Blodgett films of molecularly modified NPCOCs which are transferred onto solid substrates.

vi. Printing on solid-state or flexible substrates using an inject printer designated for printed electronics. A solution containing the NPCOCs is used as a filling material (or "ink") of the printing head according to procedures well known in the art as described in e.g. Holland et al. (*Ink Maker* 8, 83, 2005).

In various embodiments, the sensor array of the present invention comprises sensors in the form of 1D wires, 2D films, or 3D assemblies. Each possibility represents a separate embodiment of the invention. Each sensor may be configured as a chemiresistor, a chemicapacitor, a Field Effect Transistor (FET) or a combination thereof as is known in the art.

In some embodiments, the sensor or sensor array is used in conjunction with either one of a chemiresistor, a chemicapacitor, a quartz crystal microbalance, a bulk acoustic wave (BAW) and a surface acoustic wave (SAW) resonator, an electrochemical cell, a surface plasmon resonance (SPR), and an optical spectroscope. Each possibility represents a separate embodiment of the invention.

Sensing responses upon exposure of the sensor to a VOC may be induced through a change in any one or more of conductivity, resistance, impedance, capacitance, inductance, or optical properties of the sensor. Each possibility represents a separate embodiment of the invention. The sensing response can be detected using a detection means as is known in the art.

For electronically induced sensing, electrical contacts of the films of NPCOCs which were deposited on a solid substrate (e.g. silica, silicon, quartz etc) for support and/or easy array integration, can be performed by methods well known in the art. Suitable methods for inducing electrical contacts include, but are not limited to, photolithography, e-beam lithography, Focused Ion Beam (FIB), direct evaporation/sputtering through shadow mask, soft (stamp) contact, inject printing techniques of conductive nanoparticles, and other similar techniques. Alternatively, films of nanoparticles can be deposited on ready-made contacts that were fabricated by the either one of the methods described hereinabove. The electrodes, according to the principles of the present invention, can be contacted at various geometries in manners well known to a skilled artisan. In one embodiment, electrodes are contacted with a distance of about 15 µm between adjacent electrodes. In another embodiment, electrodes are contacted with a distance of about 100 µm between adjacent electrodes. According to the principles of the present invention, the distance between two adjacent electrodes is in the range of about 100 nm to about 5000 µm.

In specific embodiments, sensing can be detected through changes in the optical properties of the sensor network. In exemplary embodiments, sensing is carried out using spectroscopic ellipsometry. This technique measures the change in polarization upon reflection of polarized light from a surface. Without being bound by any theory or mechanism of action, the adsorption of analyte molecules induces changes in thickness of layers of NPCOCs networks. The change in thickness or roughness induces changes in polarization which can be recorded by the spectroscopic ellipsometry technique. The signal obtained is subsequently conveyed to a learning and pattern recognition analyzer to generate a result. In this manner no electrical contacts are required. The aggregation and/or swelling of NPCOCs upon analyte absorption render this technique advantageous for detecting volatiles with very high sensitivity.

The method of the present invention comprises exposing the at least one sensor to a test sample, and measuring a response or a plurality of responses from which a plurality of response induced parameters are extracted. Said plurality of parameters generates a plurality of patterns which are then conveyed to a learning and pattern recognition analyzer which utilizes an algorithm in order to analyze the signal patterns by comparing them to stored data.

In one embodiment, the step of measuring a plurality of response induced parameters comprises measuring a change in any electrical property such as, but not limited to the resistance, impedance, capacitance, inductance, conductivity, or optical properties of the sensor upon exposure to a test sample using a detection means and extracting a plurality of response induced parameters from said response. A response induced parameter includes, but is not limited to, steady state normalized response, the time interval for obtaining steady state normalized response, and the time required to reach baseline after removal of the test sample. Exemplary response induced parameters include, but are not limited to, full non steady state response at the beginning of the signal, full non steady state response at the beginning of the signal normalized to baseline, full non steady state response at the middle of the signal, full non steady state response at the middle of the signal normalized to baseline, full steady state response, full steady state response normalized to baseline, area under non steady state response, area under steady state response, the gradient of the response upon exposure to the test sample, the gradient of the response upon removal of the test sample, the time required to reach a certain percentage of the response, such as the time required to reach 10%, 20%, 30%, 40%, 50%, 60%, 70%, 80%, 90% or 100% of the response upon exposure to the test sample, and the time required to reach a certain percentage of the response, such as the time required to reach 100%, 90%, 80%, 70%, 60%, 50%, 40%, 30%, 20% or 10% of the response upon removal of the test sample. Each possibility represents a separate embodiment of the invention.

In another embodiment, the step of measuring a plurality of response induced parameters comprises measuring a plurality of responses selected from resistance, impedance, capacitance, inductance, conductivity, and optical properties of the sensor upon exposure to a test sample. Each possibility represents a separate embodiment of the invention.

In yet another embodiment, the step of measuring a plurality of response induced parameters comprises measuring a change in the resistance, impedance, capacitance, inductance, conductivity, or optical properties of the sensor upon exposure to a test sample and fitting the response to a function or a plurality of functions whereby the response induced parameters are selected from function constants, function coefficients and a combination thereof. Each possibility represents a separate embodiment of the invention.

In alternative embodiments, the step of measuring a plurality of response induced parameters comprises measuring a change in the resistance, impedance, capacitance, inductance, conductivity, or optical properties of the sensor upon exposure to a test sample and processing the signal (normalization, calibration etc) followed by the extraction of the plurality of response induced parameters.

According to the principles of the present invention, the plurality of response induced parameters generates a plurality of response patterns which are analyzed using a learning and pattern recognition algorithm. The analysis comprises the comparison of the plurality of response patterns to a control pattern whereby significantly different response patterns of the test sample as compared the control sample is indicative of cancer or a malignant or benign tumor.

The term "significantly different" as used herein refers to a statistically significant quantitative difference between the patterns of the test samples and the pattern of a control sample. A statistically significant difference can be determined by any test known to the person skilled in the art.

Common tests for statistical significance include, among others, t-test, ANOVA1 Kruskal-Wallis, Wilcoxon, Mann-Whitney and odds ration. Individual samples (of unknown status) can be compared with data from the reference group (negative control), and/or compared with data obtained from a positive control group known to have cancer. A statistically significant elevation or reduction in the particular response parameter being measured between the test and control sample qualifies as significant difference. A set of control samples or response patterns (positive, negative as well as those obtained from subjects known to have different grades of a benign or malignant tumor, and subjects known to have different stages of cancer) can be stored as a reference collection of data for multiple analyses. It will be recognized by one of skill in the art that the determination of whether a test subject is afflicted with cancer or has a malignant or benign tumor, as well as the determination of the cancer or tumor stage or grade is performed when comparing a response induced parameter to the appropriate control. For example, if the control is a negative control then significantly different response patterns of the test sample as compared the control sample are indicative of cancer or the presence of a malignant tumor. Conversely, if the control is a positive control then significantly different response patterns of the test sample as compared the control sample are indicative of lack of cancer or the presence of a benign tumor.

According to the principles of the present invention, the analysis is performed using a learning and pattern recognition algorithm.

Algorithms for sample analysis include, but are not limited to, principal component analysis, Fischer linear analysis, neural network algorithms, genetic algorithms, fuzzy logic pattern recognition, and the like. After analysis is completed, the resulting information can, for example, be displayed on display, transmitted to a host computer, or stored on a storage device for subsequent retrieval.

Many of the algorithms are neural network based algorithms. A neural network has an input layer, processing layers and an output layer. The information in a neural network is distributed throughout the processing layers. The processing layers are made up of nodes that simulate the neurons by the interconnection to their nodes.

When a neural network is combined with a sensor array, the sensor data is propagated through the networks. In this manner, a series of vector matrix multiplications are performed and unknown analytes can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In some embodiments, the Fisher linear discriminant analysis (FLDA) and canonical discriminant analysis (CDA) as well as combinations thereof are used to compare the output signature and the available data from the database. Each possibility represents a separate embodiment of the invention.

Multidimensional data analysis of the signals collected from all the sensors in the array can be performed using standard principle component analysis (PCA). PCA is an effective method to reduce multidimensional data space to its main components by determining the linear combinations of the sensor values such that the maximum variance between all data points can be obtained in mutually orthogonal dimensions. The first principle component provides the largest variance between sensor values. The second, third, forth, etc. principal components provide decreasing magnitudes of variance between all data points.

In particular, PCA involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

PCA compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal, components in common, but their eigenvalues differ. The mathematical technique used in principal component analysis is called eigenanalysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

An additional pattern recognition algorithm within the scope of the present invention is support vector machine (SVM). SVM performs classification by constructing an N-dimensional hyperplane that optimally separates the data into two categories. SVM models are closely related to neural networks. Using a kernel function, SVM models are alternative training methods for polynomial, radial basis function and multi-layer perceptron classifiers in which the weights of the network are found by solving a quadratic programming problem with linear constraints, rather than by solving a non-convex, unconstrained minimization problem as in standard neural network training. Using an SVM model with a sigmoid kernel function is equivalent to a two-layer, perceptron neural network.

Using the SVM model, a predictor variable is called an attribute, and a transformed attribute that is used to define the hyperplane is called a feature. The task of choosing the most suitable representation is known as feature selection. A set of features that describes one case (i.e., a row of predictor values) is called a vector. The output of SVM modeling provides the optimal hyperplane that separates clusters of vectors in a manner that affords cases with one category of the target variable on one side of the plane and cases with the other category on the other size of the plane. The vectors near the hyperplane are the support vectors.

The present invention provides an ex-vivo method of diagnosis, prognosis, staging and monitoring of various types of cancer as well as the discrimination between benign tumors and malignant tumors and the grading of tumors. The method comprises obtaining a sample selected from exhaled breath and/or a bodily fluid or secretion. Within the scope of the present invention is the direct exhaling of breath on the system comprising the at least one sensor as well as the collection of breath or bodily fluid or secretion into a container (e.g. inert bag) and exposing the system to the headspace of the container. The bodily fluids or secretions include, but not limited to, serum, urine, feces, vaginal discharge, sperm, saliva, and the like. Each possibility represents a separate embodiment of the invention. Although the sample may be tested as is, i.e. without a need for pre-concentration or dehumidification of the sample, it is also contemplated that the sample be measured after being collected by a breath collector apparatus. Exemplary breath collector apparatus within the scope of the present invention are those approved by the American Thoracic Society/European Respiratory Society (ATS/ERS); (Silkoff et al. *Am. J. Respir. Crit. Care Med.* 171, 2005, 912) for collecting alveolar breath. Alveolar breath is usually collected from individuals using the off-line method. However it is to be understood that breath collection directly to the device, vis-à-vis the on-line method is encompassed by the present invention. The breath collector apparatus may comprise a breath concentrator and/or a dehumidifying unit.

Breath concentrators that are within the scope of the present invention include, but are not limited to, I. Solid Phase Microextraction (SPME)—The SPME technique is based on a fiber coated with a liquid (polymer), a solid (sorbent), or combination thereof. The fiber coating extracts the compounds from the sample either by absorption (where the coating is liquid) or by adsorption (where the coating is solid). The SPME fiber is then inserted directly into the sensing device for desorption and subsequent analysis (Ouyang, et al., *Anal. Bioanal. Chem.,* 386, 2006, 1059; Coelho et al., *J. Chromatography B,* 853, 2007, 1). Suitable SPME fibers include, but are not limited to, divinylbenzene, carboxen, and polydimethylsiloxane fibers. Each possibility represents a separate embodiment of the invention II. Sorbent Tubes—Sorbent tubes are typically made of glass and contain various types of solid adsorbent material (sorbents). Commonly used sorbents include activated charcoal, silica gel, and organic porous polymers such as Tenax and Amberlite XAD resins. Sorbent tubes are attached to air sampling pumps for sample collection. A pump with a calibrated flow rate in ml/min draws a predetermined volume of air through the sorbent tube. Chemicals are trapped onto the sorbent material throughout the sampling period. This technique was developed by the US National Institute for Occupational Safety and Health (NIOSH).

III. Cryogenic Concentrations—Cryogenic condensation is a process that allows recovery of volatile organic compounds (VOCs) for reuse. The condensation process requires very low temperatures so that VOCs can be condensed. Traditionally, chlorofluorocarbon (CFC) refrigerants have been used to condense the VOCs. Currently, liquid nitrogen is used in the cryogenic (less than −160° C.) condensation process.

A dehumidifier in accordance with the present invention includes the following non-limiting examples:

I. Drawing moist air over cold refrigerated coils—using this approach, the air moisture condenses into droplets as it passes through cold refrigerated coils into a container. "Dried" air then brought to its original temperature and returned to the sensing device.

II. Silica Gel—is an amorphous form of silicon dioxide, which is synthetically produced in the form of hard irregular granules or beads. A microporous structure of interlocking cavities gives a very high surface area (800 square meters per gram). This unique structure renders the silica gel as a high capacity desiccant. Water molecules adhere to the surface of the silica gel due to its low vapor pressure as compared to the surrounding air. When pressure equilibrium is reached, the adsorption ceases. Thus the higher the humidity of the surrounding air, the greater the amount of water that is adsorbed before equilibrium is reached. Silica gel is advantageous as a drying substance since the process of drying requires no chemical reaction and no by products or side effects.

III. Activated carbon—is formed by processing charcoal to an extremely porous carbon substance. Due to its high degree of microporosity the activated carbon possesses a very large surface area available for chemical reactions. Sufficient activation may be obtained solely from the high surface area, though further chemical treatment often enhances the adsorbing properties of the material.

IV. Desiccant Molecular Sieves—are synthetically produced, highly porous crystalline metal-alumino silicates. They are classified by the many internal cavities of precise diameters, namely, 3 Å, 4 Å, 5 Å, and 10 Å. Adsorption occurs only when molecules to be adsorbed have smaller diameters than the cavity openings. Molecules of high polarity are better adsorbed into the molecular sieves. Molecular sieves adsorb water molecules and other contaminants from liquids and gases down to very low levels of concentrations, often to 1 ppm.

The breath collector apparatus may further comprise a heating/cooling unit, or a unit that monitors and stabilizes the conditions for sample maintenance (e.g. humidity, temperature, atmospheric pressure and the like).

The present invention further provides a sensor array comprising six sensors, five sensors comprising spherical Au nanoparticles capped with an organic coating and one sensor comprising cubic Pt nanoparticles capped with benzylmercaptan. In some embodiments, the present invention provides a sensor array comprising five sensors of Au nanoparticles capped with an organic coating selected from tert-dodecanethiol, 2-ethylhexanethiol, 2-mercaptobenzyl alcohol, 2-mercaptobenzoazole and calixarene, and one sensor of Pt nanoparticles capped with benzylmercaptan. In other embodiments, the present invention provides a sensor array comprising six sensors, five sensors comprising spherical Au nanoparticles capped with various organic coatings and one sensor comprising cubic Pt nanoparticles capped with benzylmercaptan. In accordance with these embodiments, each of the five sensors of Au nanoparticles is capped with a different organic coating selected from tert-dodecanethiol, 2-ethylhexanethiol, 2-mercaptobenzyl alcohol, 2-mercaptobenzoazole, and calixarene. In one embodiment, the present invention provides a sensor array consisting of six sensors as follows: (1) a sensor of Au nanoparticles capped with tert-dodecanethiol, (2) a sensor of Au nanoparticles capped with 2-ethylhexanethiol, (3) a sensor of Au nanoparticles capped with 2-mercaptobenzyl alcohol, (4) a sensor of Au nanoparticles capped with 2-mercaptobenzoazole, (5) a sensor of Au nanoparticles capped with calixarene, and (6) a sensor of Pt nanoparticles capped with benzylmercaptan. The sensor array may further comprise a detection means. In further embodiments, the sensor array may comprise a learning and pattern recognition analyzer wherein the learning and pattern recognition analyzer receives sensor signal output patterns and compares them to stored data. It is contemplated that this sensor array and system are particularly advantageous for detecting volatile organic compounds indicative of a breast tumor selected from a benign tumor and a malignant tumor.

As used herein and in the appended claims the singular forms "a", "an," and "the" include plural references unless the content clearly dictates otherwise. Thus, for example, reference to "an organic coating" includes a plurality of such organic coatings and equivalents thereof known to those skilled in the art, and so forth.

The principles of the present invention are demonstrated by means of the following non-limiting examples.

EXAMPLES

Example 1: Collection of Exhaled Breath

After deep exhaling, subjects inhaled to total lung capacity through a mouthpiece that contained a cartridge on the aspiratory port, in order to remove more than 99.99% of VOC ambient contaminants from inhaled air during inspiration. Subjects then exhaled against 10-15 cm of $H_2O$ pressure to ensure closure of the vellum to exclude nasal entrainment of gas. Exhaled gas was collected through a separate exhalation port of the mouthpiece in a non-reactive Mylar gas-sampling bag (purchased from Eco Medics), which was previously cleaned with $N_2$ gas. Two Mylar bags were collected from each subject. The samples were collected and analyzed during a period of approximately 4 months.

Example 2: Test Population

Breath samples were taken from 25 healthy women and 17 women with breast cancer at the ages of 26-73 after signed consent. All experiments were performed according to the guidelines of the Technion's committee for supervision of human experiments (Haifa, Israel). Four women (two of each population) were excluded from further testing due to technical problems. The healthy population was defined as women whose mammography testing showed no signs of tumor/s or alternatively women whose mammography testing showed benign tumor/s (confirmed by biopsies). The breast cancer (BC) population was defined as women with abnormal mammography results that were further confirmed to be malignant using biopsy and/or pathological examination after surgical removal of the tumor. None of the patients received chemotherapy and/or other cancer treatment prior to the breath testing. The clinical characteristics of the studied populations are listed in table 1.

TABLE 1

Clinical characteristics of 15 breast cancer patients and 23 healthy controls at the ages of 26-73 which were tested in this study. All volunteers were female. No inclusion/exclusion criteria were applied in this group of volunteers.

| Classification | Diagnosis (Histology/ Mammography) | TNM.[1] Stage | Stage (Total) | Age | Smoker (Y/N) | Family cancer history (Y/N) | Additional data |
|---|---|---|---|---|---|---|---|
| Healthy with clear mammography | No tumors | NA.[2] | NA | 48 | N | Y | n/a.[3] |
| | No tumors | | | 26 | N | n/a | n/a |
| | No tumors | | | 44 | Y | N | Under medication |
| | No tumors | | | 56 | Y | Y | Under medication for high cholesterol levels |
| | No tumors | | | 49 | N | N | Allergic to Penicillin and Optalgin (Dypyrone) |
| | No tumors | | | 53 | N | Y | n/a |
| | No tumors | | | 55 | N | Y | n/a |
| Healthy with benign breast conditions | Benign | | | 51 | n/a | n/a | n/a |
| | Benign | | | 57 | n/a | n/a | n/a |
| | Benign | | | 53 | N | N | n/a |
| | Benign | | | 60 | Y | Y | Takes Indomethacin against artery inflammations; takes food additives. |
| | Benign | | | 63 | N | Y | High blood pressure; thyroid gland problems; osteoporosis; allergic to Penicillin; exposure to asbestos; takes Eltroxin, Actonel, medicine for high blood pressure, vitamin D and calcium. |
| | Benign | | | 50 | N | Y | Allergic to dust and Penicillin. |
| | Benign | | | 51 | Y | Y | Kidney stones; thyroid gland problems; asbestos exposure; Takes Losec, Eltroxin, iron and vitamin D. |

TABLE 1-continued

Clinical characteristics of 15 breast cancer patients and 23 healthy controls at the ages of 26-73 which were tested in this study. All volunteers were female. No inclusion/exclusion criteria were applied in this group of volunteers.

| Classification | Diagnosis (Histology/ Mammography) | TNM.[1] Stage | Stage (Total) | Age | Smoker (Y/N) | Family cancer history (Y/N) | Additional data |
|---|---|---|---|---|---|---|---|
| | Benign tumor | | | 49 | N | N | Takes Deralin for high blood pressure and vitamin D. |
| | Benign tumor | | | 54 | Y | Y | High cholesterol; diabeties. |
| | Benign tumor | | | 63 | N | Y | Allergic to acrylics; takes food additives and glycerin. |
| | Benign tumor | | | 58 | N | N | High blood pressure; takes aspirin and Normiten. |
| | Benign tumor | | | 47 | N | N | n/a |
| | Benign tumor | | | 47 | Y | N | Takes vitamins. |
| | Benign tumor | | | 68 | N | Y | Takes drugs for high blood pressure; osteoporosis; artery calcification. Allergic to mustard; takes vitamin D |
| | Benign tumor | | | 73 | N | n/a | Diabeties, high blood pressure, renal illness, Hyperlipidemia. Takes several medicines on daily basis. |
| | Benign tumor | | | 47 | N | n/a | n/a |
| DCIS.[4] | DCIS | T0TisN0M0 | 0 | 51 | Y | Y | Exposure to asbestos. Takes medications for allergy. |
| | DCIS | T0TisN0M0 | 0 | 51 | N | n/a | Exposed to asbestos on daily basis; Takes Sabril on regular basis. |
| IDC.[5] | IDC Grade 1 | T1amN0M0 | I | 58 | Y | Y | Takes vitamin C and minerals |
| | IDC | n/a | | 50 | N | Y | Takes vitamins (E). |
| | IDC Grade 1 | T1cN0M0 | I | 62 | N | Y | Takes medicine Losec and vitamin D on regular basis. |
| | IDC Grade 2 | T1bN1micM0 | IIa | 62 | N | Y | n/a |
| | IDC Grade 2 | T1cN0M0 | I | 46 | N | N | High blood pressure; allergic to penicillin and calcium; takes medicine Cardiloc and Lipitor. |
| | IDC Grade 2 | T2N0M0 | IIa | 66 | N | Y | n/a |
| | IDC Grade 3 | T4cN2M1 | IV | 61 | N | N | n/a |
| | IDC Grade 3 | T2N1M0 | IIb | 55 | N | n/a | Takes medication for high cholesterol levels. |
| | IDC Grade 2 | T1cN2M0 | IIIa | 49 | N | n/a | Exposed to detergents and cleaning agents on daily basis |
| | IDC Grade 2 | 4(T4N1M1) | IV | 57 | N | n/a | Takes medicine for high blood pressure and diabetes. Had surgery for removal of uterus |

TABLE 1-continued

Clinical characteristics of 15 breast cancer patients and 23 healthy controls at the ages of 26-73 which were tested in this study. All volunteers were female. No inclusion/exclusion criteria were applied in this group of volunteers.

| Classification | Diagnosis (Histology/ Mammography) | TNM.[1] Stage | Stage (Total) | Age | Smoker (Y/N) | Family cancer history (Y/N) | Additional data |
|---|---|---|---|---|---|---|---|
| n/a | Invasive carcinoma with mucin production | T3N1M0 | IIIa | 47 | N | n/a | n/a§ |
| Non Ductal Carcinoma | Invasive lobular carcinoma | T3N?M0 | IIb/IIIa | 41 | n/a | n/a | n/a§ |
|  | Tubular carcinoma | T1bN0M0 | I | 47 | Y | Y | n/a |

[1]T = Tumor Size; N = Lymph Node Status; and M = Distant Metastases graded 0-4.
[2]NA = not applicable
[3]n/a = not available
[4]DCIS = Ductal Carcinoma In situ
[5]IDC = Invasive Duct Carcinoma Example 3: Synthesis and Capping of Gold and Platinum Nanoparticles Gold nanoparticles having an average size of about 5 nm were capped with different organic molecules (Tert-dodecanethiol, 2-Ethylhexanethiol, 2-Mercaptobenzyl alcohol, 2-Mercaptobenzoazole, and Calixarene). Gold nanoparticles capped with thiols were synthesized using the standard two-phase method according to Brust et al. (*J. Chem. Soc., Chem. Corn.*, 801, 1994, 2), with some modifications according to Hostetler et al. (*Langmuir*, 1998, 14, 24). Briefly, $AuCl_4^-$ was first transferred from aqueous $HAuCl_4 \cdot xH_2O$ solution (25 ml, 31.5 mM) to a toluene solution by the phase-transfer reagent TOAB (80 ml, 34.3 mM). After the organic phase was isolated, excess of the thiols was added to the solution. The mole ratio of thiol: $HAuCl_4 \cdot xH_2O$ varied between 1:1 and 10:1 depending on the thiol used, in order to prepare monodispersed solution of gold nanoparticles having an average size of about 5 nm. After vigorous stirring of the solution for 10 min, aqueous solution of reducing agent $NaBH_4$ in large excess (25 mL, 0.4 M, ice-cooled) was added. The reaction was stirred at room temperature for at least 3 hours, which produced a dark brown solution of the thiol-capped gold nanoparticles. The resulting solution was subjected to solvent removal in a rotary evaporator followed by multiple washings using ethanol and toluene.

Gold nanoparticles capped with mercaptols were synthesized by the ligand—exchange method from pre-prepared hexanethiol-capped gold nanoparticles. In a typical reaction, excess of incoming mercaptol (7 μg) was added to a solution of hexanethiol-capped gold nanoparticles in toluene (3 mg/ml, 5 ml). The solution was subjected to constant stirring for few days in order to allow maximal ligand conversion. The nanoparticles were purified from free thiol ligands by repeated extractions.

Gold nanoparticles capped with calixarenes were synthesized as described herein above using calixarenes and $HAuCl_4 \cdot xH_2O$ in a mole ratio of [0.25]:[1].

Cubic platinum nanoparticles capped with benzylmercaptan were synthesized according to the following procedure. In a typical synthesis, 0.028 g (0.071 mmol, 3.6 mM) of platinum precursor, platinum acetylacetonate was dissolved in 20 ml of toluene, followed by the addition of 13 equiv. of ODA as the surfactant. The platinum precursor was then decomposed under a hydrogen pressure of 3 bar at 55° C. in a pressure reaction vessel (Fischer-Porter bottle) for 20 h. The Pt nanoparticles that precipitated in the reaction bottle were collected by centrifuging and dissolved in dichloromethane solvent.

The capping of the cubic Pt nanoparticles was performed using the ligand exchange method from pre-prepared ODA-capped cubic Pt nanoparticles with corresponding capping ligands in dichloromethane solvents. In particular, an excess of incoming benzylmercaptan was added to the solution of ODA-capped cubic Pt nanoparticles in dichloromethane (3 ml). After few days of exchange reaction the Pt nanoparticles were washed through repeated ultrasonic redispersion-centrifugation followed by dissolution in dichloromethane.

Example 4: Sensor Fabrication

Interdigitated electrodes are firstly patterned or deposited on top of the degenerative p-doped silicon wafer having 300 nm (in thickness) $SiO_2$ film, using either lithography process or evaporation of metal through a shadow mask.

In particular, functionalized gold or platinum nanoparticles (table 2) having an average diameter of about 5 nm for the Au nanoparticles and 20 nm for the Pt nanoparticles, were dispersed in toluene by sonication, followed by a drop of the nanoparticles solution cast into the electrode. While still coated with solution, the substrate was blown with a stream of dry $N_2$. This process was repeated several times to yield the desired resistance, preferably from 20 KSS to 5 MΩ. In other experiments, film resistances from 100Ω to 80 MΩ were prepared. The device was dried for 2 hours in a fume hood at an ambient temperature, and then heated to 50° C. in a vacuum oven over night.

TABLE 2

Sensor array.

| Nanoparticles | Functional molecules |
|---|---|
| Au | Tert-dodecanethiol |
| Au | 2-Ethylhexanethiol |

TABLE 2-continued

Sensor array.

| Nanoparticles | Functional molecules |
|---|---|
| Au | 2-Mercaptobenzyl alcohol |
| Au | 2-Mercaptobenzoazole |
| Au | Calixarene |
| Pt | Benzylmercaptan |

The developed sensors were mounted onto a custom PTFE circuit board which had 40 separated sensor sites. The board was then mounted onto a stainless steel test chamber having a volume of less than 400 cm$^3$. An Agilent Multi-function switch 34980 controlled by USB was used to choose the active sensor and measure the corresponding resistance at a given time. The entire system was controlled by a custom Labview program.

Example 5: Response of a Single Sensor of Cubic Pt Nanoparticles Capped with Benzylmercaptan to Breath Samples The responses of a single sensor of cubic Pt nanoparticles capped with benzylmercaptan to the breath samples of 38 women (23 healthy and 15 BC=breast cancer; table 1) were analyzed using principle component analysis (PCA). Particularly, four response induced parameters (features) were measured and analyzed using the PCA technique. The four response induced parameters used were: $\Delta R$ start (full response at the beginning of the signal), $\Delta R/R$ start (response normalized to baseline at the beginning of the signal), $\Delta R$ middle (full response at the middle of the signal), and gradient base edge (gradient of resistance change upon removal of the breath sample).

FIG. 1 shows the separation of breath samples of healthy population and BC population using only one principle component. Two healthy subjects were misclassified as BC and vice versa. The sensitivity is thus ~87% (13/15) for BC and ~91% (21/23) for healthy. Student's t-test ($\alpha=0.05$) showed distinct averages with P<0.001.

Figure 2:
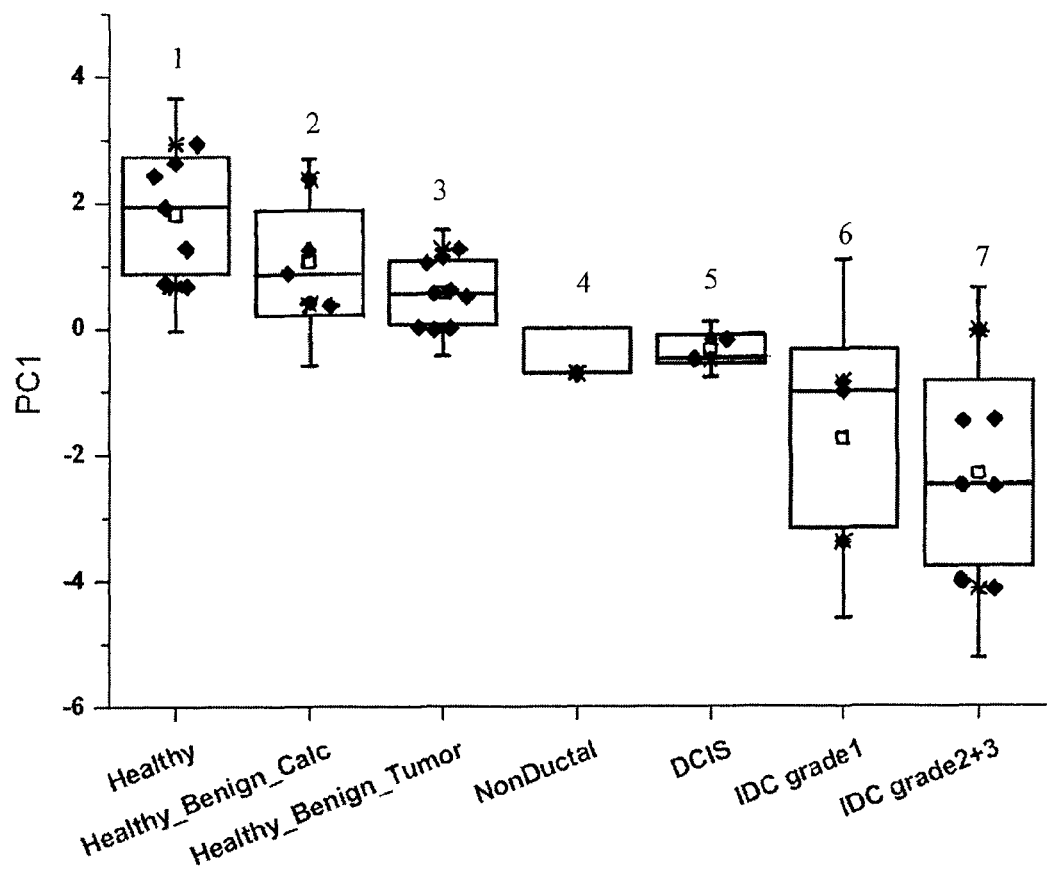
FIG. 2. Staging of 34 subjects according to the severity of the disease using a single sensor and four response induced parameters. (1) healthy, (2) healthy subjects with some benign irregularities in their mammography, (3) healthy subjects with benign tumors, (4) Non-ductal carcinoma, (5) Ductual Carcinoma In situ, (6) Invasive Duct Carcinoma grade 1, and (7) Invasive Duct Carcinoma grade 2 and grade 3.

A more refined classification according to sub-populations (four misclassifications removed) showed that the PC1 values correlate with the stage of the breast cancer as well as with the classifications of healthy populations. FIG. 2, demonstrates the classification to seven sub-groups. Patients with Invasive Duct Carcinoma of grads 2 and 3 have the lowest PC1 values (square 7; FIG. 2), patients with Invasive Duct Carcinoma of grad 1 (initial stage Infiltrating Ductal Carcinoma) have higher PC1 values (square 6; FIG. 2), patients with Ductal Carcinoma In Situ (DCIS; a stage zero cancer) and patients with non ductal carcinomas have higher PC1 values (squares 5 and 4, respectively; FIG. 2), healthy subjects that were found to have a tumor but the tumor was considered benign and non-cancerous have even higher PC1 values (square 3; FIG. 2), healthy subjects with some (benign) irregularities in their mammography have even higher PC1 values (square 2; FIG. 2), and healthy subjects whose screening showed no tumors or lumps have the highest PC1 values (square 1; FIG. 2). Of note is that the PC1 values and signs may vary in different analyses but the relative values in a single analysis are consistent. Student's t-tests ($\alpha=0.05$; table 3) were performed to determine the statistical significance of the separation to the different sub-populations. Of note are sub-groups #4 and #5 each containing two subjects thus providing large STD error and relatively high P-values.

TABLE 3

Statistical analysis of the differentiation into seven sub-groups using a single sensor with four features.

| 1$^{st}$ sub-population | 2$^{nd}$ sub-population | Difference | Lower CL | Upper CL | p-Value |
|---|---|---|---|---|---|
| Healthy | IDC grade2 + 3 | 4.102046 | 3.01006 | 5.194031 | <.0001 |
| Healthy | IDC grade1 | 3.555312 | 2.14557 | 4.965059 | <.0001 |
| Healthy_Benign_Calc | IDC grade2 + 3 | 3.347522 | 2.15131 | 4.543732 | <.0001 |
| Healthy_Benign_Tumor | IDC grade2 + 3 | 2.864301 | 1.83477 | 3.893834 | <.0001 |
| Healthy_Benign_Calc | IDC grade 1 | 2.800789 | 1.30885 | 4.292724 | 0.0007 |
| Healthy | NonDuctal | 2.510546 | 0.32658 | 4.694516 | 0.0258 |
| Healthy_Benign_Tumor | IDC grade1 | 2.317568 | 0.95562 | 3.679512 | 0.0017 |
| Healthy | DCIS | 2.139566 | 0.50159 | 3.777543 | 0.0124 |
| DCIS | IDC grade2 + 3 | 1.96248 | 0.3245 | 3.600457 | 0.0207 |
| Healthy_Benign_Calc | NonDuctal | 1.756022 | −0.48188 | 3.993925 | 0.119 |
| NonDuctal | IDC grade2 + 3 | 1.5915 | −0.59247 | 3.77547 | 0.1465 |
| DCIS | IDC grade1 | 1.415747 | −0.44917 | 3.280666 | 0.131 |
| Healthy_Benign_Calc | DCIS | 1.385042 | −0.32418 | 3.094269 | 0.1079 |
| Healthy_Benign_Tumor | NonDuctal | 1.272801 | −0.88062 | 3.426225 | 0.2357 |
| Healthy | Healthy_Benign_Tumor | 1.237745 | 0.20821 | 2.267278 | 0.0203 |
| NonDuctal | IDC grade1 | 1.044767 | −1.31419 | 3.403724 | 0.3715 |
| Healthy_Benign_Tumor | DCIS | 0.901821 | −0.6952 | 2.498843 | 0.2567 |
| Healthy | Healthy_Benign_Calc | 0.754524 | −0.44169 | 1.950733 | 0.2066 |
| IDC grade1 | IDC grade2 + 3 | 0.546733 | −0.86301 | 1.95648 | 0.4331 |
| Healthy_Benign_Calc | Healthy_Benign_Tumor | 0.483221 | −0.65626 | 1.622705 | 0.3919 |
| DCIS | NonDuctal | 0.37098 | −2.13107 | 2.873032 | 0.7633 |

Figure 3:
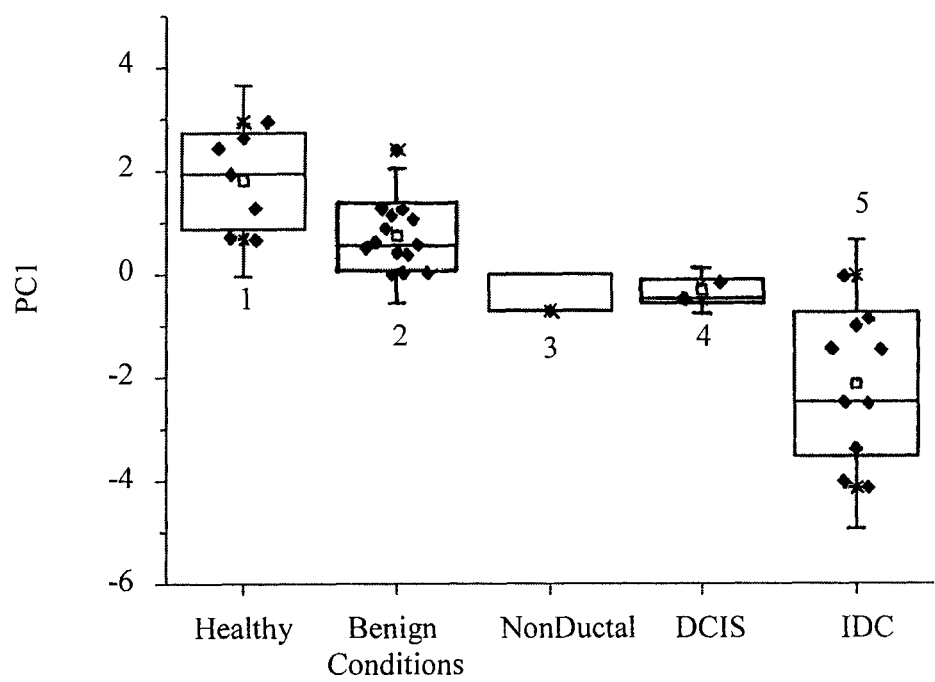
FIG. 3. Staging of 34 subjects according to the severity of the disease using a single sensor and four response induced parameters. (1) healthy, (2) benign conditions (3) Non-ductal carcinoma, (4) Ductual Carcinoma In situ, (5) Invasive Duct Carcinoma grades 1-3.

Classification of the data to five groups: healthy (1), benign conditions (2), Non-ductal carcinoma (3), Ductal Carcinoma In Situ (4), and Invasive Duct Carcinoma grades 1-3 (5) is shown in FIG. 3. Student's t-tests ($\alpha$=0.05) to determine the statistical significance of the separation to the different sub-populations is presented in table 4. Of note are sub-groups #3 and #4 each containing two subjects thus providing large STD error and relatively high P-values.

TABLE 4

Statistical analysis of the differentiation into five sub-groups using a single sensor with four features.

| 1$^{st}$ sub-population | 2$^{nd}$ sub-population | Difference | Lower CL | Upper CL | p-Value |
|---|---|---|---|---|---|
| Healthy | IDC | 3.938026 | 2.94511 | 4.930943 | <.0001 |
| Benign Conditions | IDC | 2.87286 | 2.03864 | 3.707077 | <.0001 |
| Healthy | NonDuctal | 2.510546 | 0.35661 | 4.664485 | 0.0239 |
| Healthy | DCIS | 2.139566 | 0.52411 | 3.75502 | 0.0112 |
| DCIS | IDC | 1.79846 | 0.23778 | 3.359137 | 0.0254 |
| Benign Conditions | NonDuctal | 1.44538 | −0.64016 | 3.530923 | 0.167 |
| NonDuctal | IDC | 1.42748 | −0.68569 | 3.540647 | 0.1777 |
| Benign Conditions | DCIS | 1.0744 | −0.44866 | 2.597465 | 0.1598 |
| Healthy | Benign Conditions | 1.065166 | 0.13248 | 1.997849 | 0.0266 |
| DCIS | NonDuctal | 0.37098 | −2.09667 | 2.838627 | 0.7607 |

Hence, evaluating the magnitude of the PC1 values provides refined separation, not only to healthy and BC populations but further to the different stages of the disease using a single sensor and four response induced parameters.

Example 6: Response of the Sensor Array to Breath Samples

The responses of the six sensors of Example 4 to the breath samples of 38 women (23 healthy and 15 BC=breast cancer) were analyzed using principle component analysis (PCA). Particularly, seven response induced parameters (features) were measured and analyzed from each sensor, yielding a total of 42 features from the 6 different sensors that were analyzed using the PCA technique. The seven response induced parameters used were: $\Delta R$ start (full response at the beginning of the signal), $\Delta R/R$ start (response normalized to baseline at the beginning of the signal), $\Delta R$ middle (full response at the middle of the signal), $\Delta R/R$ middle (response normalized to baseline at middle of the signal), $\Delta R$ end (full response at the end of the signal), $\Delta R/R$ end (response normalized to baseline at the end of the signal), and gradient base edge (gradient of resistance change upon removal of the breath sample).

Figure 4:
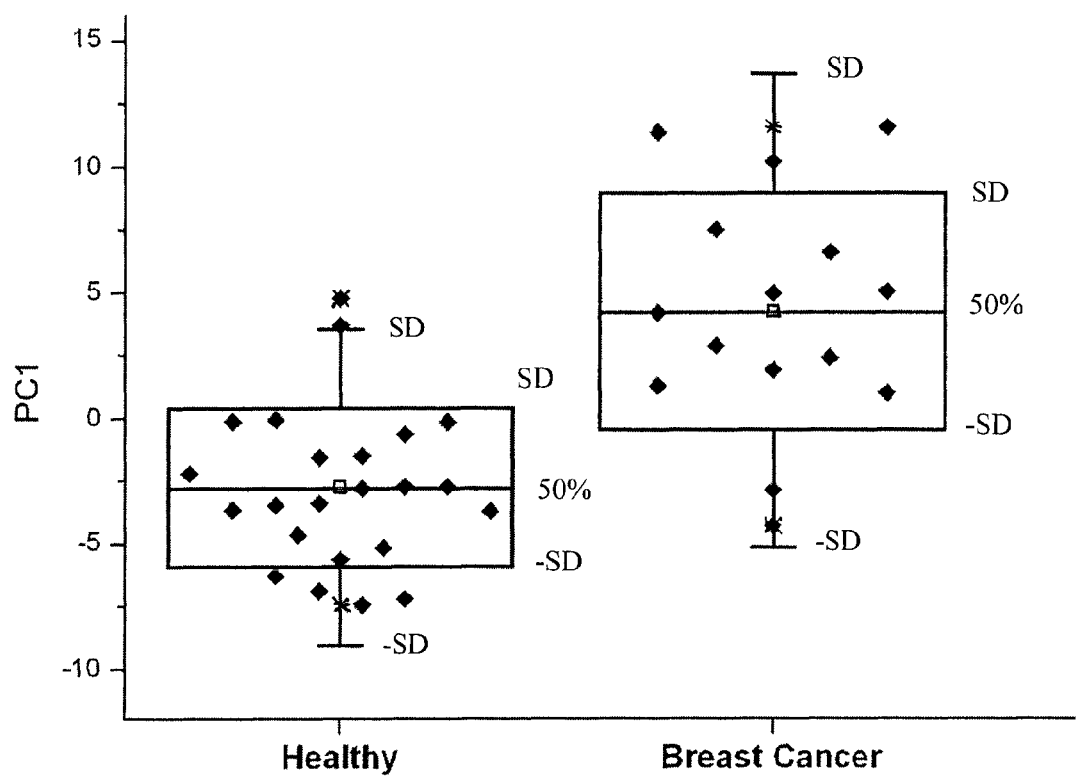
FIG. 4. Separation to healthy and BC populations using an array of six sensors and seven response induced parameters.

FIG. 4 shows the separation of breath samples of healthy population (negative PC1 values) and BC population (positive PC1 values) using only one principle component. Of note is that the PC1 values and signs may vary in different analyses but the relative values in a single analysis are consistent. Two healthy subjects were misclassified as BC and vice versa. The sensitivity is thus ~87% (13/15) for BC and ~91% (21/23) for healthy. Student's t-test ($\alpha$=0.05) showed distinct averages with P<0.001.

Figure 5:
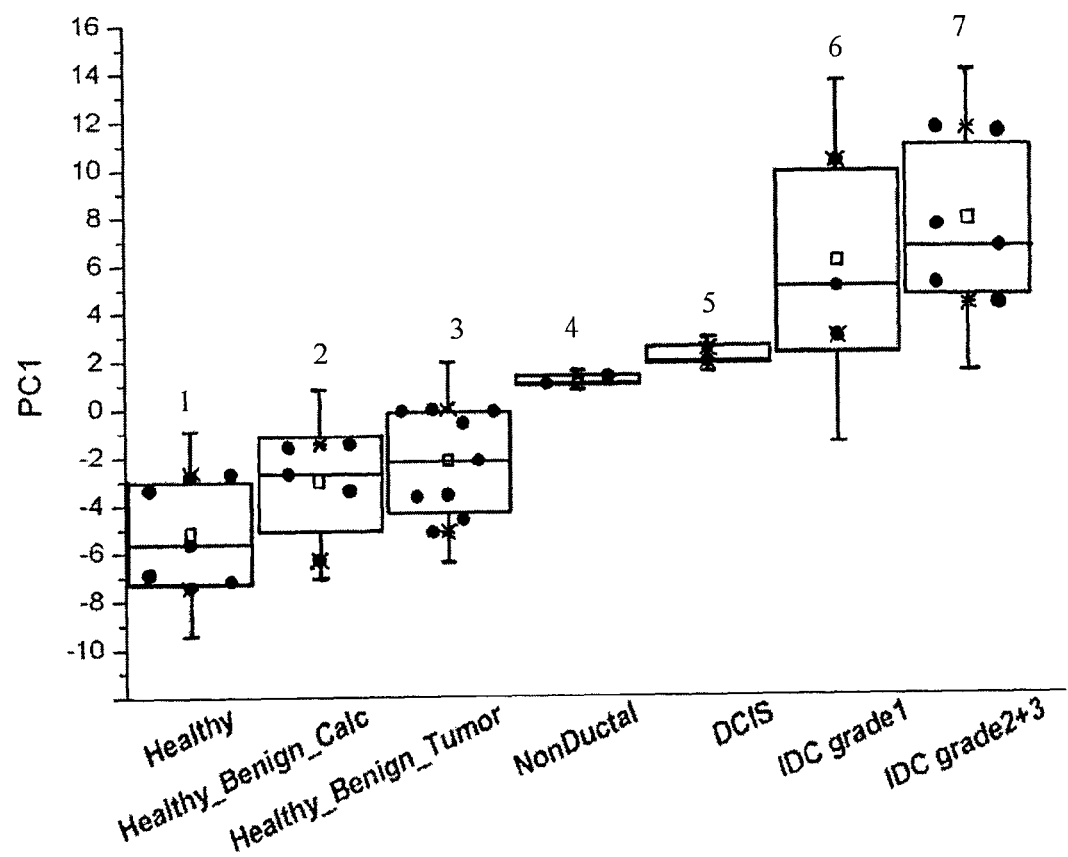
FIG. 5. Staging of 34 subjects according to the severity of the disease using an array of six sensors and seven response induced parameters. (1) healthy, (2) healthy subjects with some benign irregularities in their mammography, (3) healthy subjects with benign tumors, (4) Non-ductal carcinoma, (5) Ductual Carcinoma In situ, (6) Invasive Duct Carcinoma grade 1, and (7) Invasive Duct Carcinoma grade 2 and grade 3.

In addition, when examining the average PC1 values, the healthy and BC populations appear scattered (variations in the values of the PC1 component in each population; FIG. 4). The scattering in the BC population stems from variations in tumor size or stage of the disease. Thus, when drawing the PC1 values vs. the stage of the breast cancer (four misclassifications removed), a clear correlation can be viewed where patients with Invasive Duct Carcinoma of grads 2 and 3 have the highest positive PC1 values (square 7; FIG. 5), and patients with Invasive Duct Carcinoma of grad 1 (initial stage Infiltrating Ductal Carcinoma) have slightly lower PC1 values (square 6; FIG. 5). Accordingly even lower PC1 values are obtained for patients with Ductal Carcinoma In Situ (DCIS; a stage zero cancer) and patients with non ductal carcinomas (squares 5 and 4, respectively; FIG. 5). The latter have absolute mean values which are closer to zero thus being closer to the border line between healthy and BC populations. Similarly, the scattering in the healthy population (negative PC1 values) also reflects different stages: healthy subjects whose screening showed no tumors or lumps have the lowest PC1 values (square 1; FIG. 5), healthy subjects with some (benign) irregularities in their mammography results have slightly higher PC1 values (square 2; FIG. 5), and healthy subjects that were found to have a tumor but the tumor was considered benign and non-cancerous have the highest values in the negative range (square 3; FIG. 5). The values of the latter population are closer to zero and are positioned closest to the BC populations of all healthy populations. Student's t-tests ($\alpha$=0.05) to determine the statistical significance of the separation to the different sub-populations is presented in table 5. Of note are sub-groups #4 and #5 each containing two subjects thus providing large STD error and relatively high P-values.

TABLE 5

Statistical analysis of the differentiation into seven sub-groups using a six sensor array with seven features.

| 1$^{st}$ sub-population | 2$^{nd}$ sub-population | Difference | Lower CL | Upper CL | p-Value |
|---|---|---|---|---|---|
| IDC grade2 + 3 | Healthy | 12.83528 | 10.106 | 15.56457 | <.0001 |
| IDC grade1 | Healthy | 11.14369 | 7.7584 | 14.52896 | <.0001 |
| IDC grade2 + 3 | Healthy_Benign_Calc | 10.79189 | 7.8213 | 13.76245 | <.0001 |
| IDC grade2 + 3 | Healthy_Benign_Tumor | 9.9458 | 7.3603 | 12.53135 | <.0001 |
| IDC grade1 | Healthy_Benign_Calc | 9.1003 | 5.5177 | 12.68293 | <.0001 |
| IDC grade1 | Healthy_Benign_Tumor | 8.25421 | 4.9837 | 11.52469 | <.0001 |
| DCIS | Healthy | 7.30395 | 3.3706 | 11.23727 | 0.0007 |
| IDC grade2 + 3 | NonDuctal | 6.55024 | 2.5447 | 10.55575 | 0.0024 |
| NonDuctal | Healthy | 6.28504 | 2.3517 | 10.21837 | 0.0029 |
| IDC grade2 + 3 | DCIS | 5.53134 | 1.5258 | 9.53684 | 0.0086 |
| DCIS | Healthy_Benign_Calc | 5.26055 | 1.1561 | 9.36498 | 0.0139 |
| IDC grade1 | NonDuctal | 4.85865 | 0.3804 | 9.33694 | 0.0345 |
| DCIS | Healthy_Benign_Tumor | 4.41447 | 0.5795 | 8.24945 | 0.0257 |

TABLE 5-continued

Statistical analysis of the differentiation into seven sub-groups using a six sensor array with seven features.

| 1st sub-population | 2nd sub-population | Difference | Lower CL | Upper CL | p-Value |
|---|---|---|---|---|---|
| NonDuctal | Healthy_Benign_Calc | 4.24165 | 0.1372 | 8.34607 | 0.0433 |
| IDC grade1 | DCIS | 3.83974 | −0.6385 | 8.31804 | 0.0899 |
| NonDuctal | Healthy_Benign_Tumor | 3.39556 | −0.4394 | 7.23054 | 0.0804 |
| Healthy_Benign_Tumor | Healthy | 2.88948 | 0.4172 | 5.36173 | 0.0237 |
| Healthy_Benign_Calc | Healthy | 2.04339 | −0.8291 | 4.91589 | 0.1559 |
| IDC grade2 + 3 | DC grade1 | 1.69159 | −1.7773 | 5.16046 | 0.3259 |
| DCIS | NonDuctal | 1.01891 | −3.8868 | 5.92463 | 0.6734 |
| Healthy_Benign_Tumor | Healthy_Benign_Calc | 0.84609 | −1.8902 | 3.58237 | 0.5311 |

Figure 6:
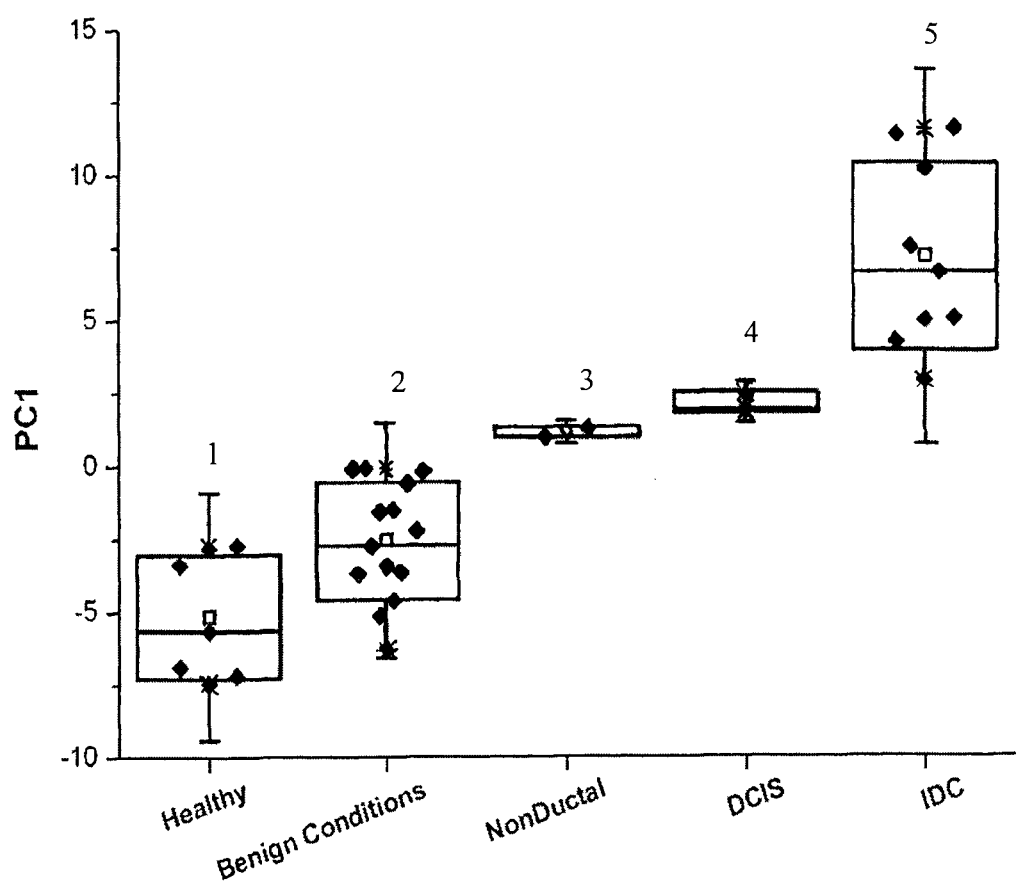
FIG. 6. Staging of 34 subjects according to the severity of the disease using an array of six sensors and seven response induced parameters. (1) healthy, (2) benign conditions (3) Non-ductal carcinoma, (4) Ductual Carcinoma In situ, (5) Invasive Duct Carcinoma grades 1-3.

Classification of the data to five groups: healthy (1), benign conditions (2), Non-ductal carcinoma (3), Ductal Carcinoma In Situ (4), and Invasive Duct Carcinoma grades 1-3 (5) is shown in FIG. 6. Student's t-tests ($\alpha=0.05$) to determine the statistical significance of the separation to the different sub-populations is presented in table 6. All populations except DCIS and Non Ductal carcinoma are differentiated with $P<0.05$.

TABLE 6

Statistical analysis of the differentiation into five sub-groups using a six sensor array with seven features.

| 1st sub-population | 2nd sub-population | Difference | Lower CL | Upper CL | p-Value |
|---|---|---|---|---|---|
| IDC | Healthy | 12.27142 | 9.83259 | 14.71025 | <.0001 |
| IDC | Benign Conditions | 9.68411 | 7.61649 | 11.75173 | <.0001 |
| DCIS | Healthy | 7.30395 | 3.42379 | 11.1841 | 0.0006 |
| NonDuctal | Healthy | 6.28504 | 2.40489 | 10.1652 | 0.0025 |
| IDC | NonDuctal | 5.98638 | 2.20324 | 9.76951 | 0.003 |
| IDC | DCIS | 4.96747 | 1.18434 | 8.75061 | 0.0119 |
| DCIS | Benign Conditions | 4.71664 | 1.05839 | 8.37489 | 0.0133 |
| NonDuctal | Benign Conditions | 3.69774 | 0.03949 | 7.35598 | 0.0477 |
| Benign Conditions | Healthy | 2.58731 | 0.3471 | 4.82751 | 0.0251 |
| DCIS | NonDuctal | 1.01891 | −3.8205 | 5.85831 | 0.6699 |

Hence, evaluating the magnitude of the PC1 values provides refined separation, not only to healthy and BC populations but further to the different stages of the disease. Using the sensor array of the present invention together with pattern recognition analysis provides the diagnosis of breast cancer for population screening and further provides the diagnosis of the breast cancer stage and other related information such as the presence of benign breast tumors which may develop into malignant tumors. The results clearly show that the values of the PC1 component allow the separation of populations into groups of healthy and BC and further separation of these groups into sub-groups reflecting different stages of health.

Example 7: the Effect of Using a Plurality of Response Induced Parameters on the Analysis In order to evaluate the effect of using multiple parameters of sensor response per each sensor on the sensitivity and selectivity of the analysis, the experiments were repeated with varied numbers of response induced parameters.

Figure 7:
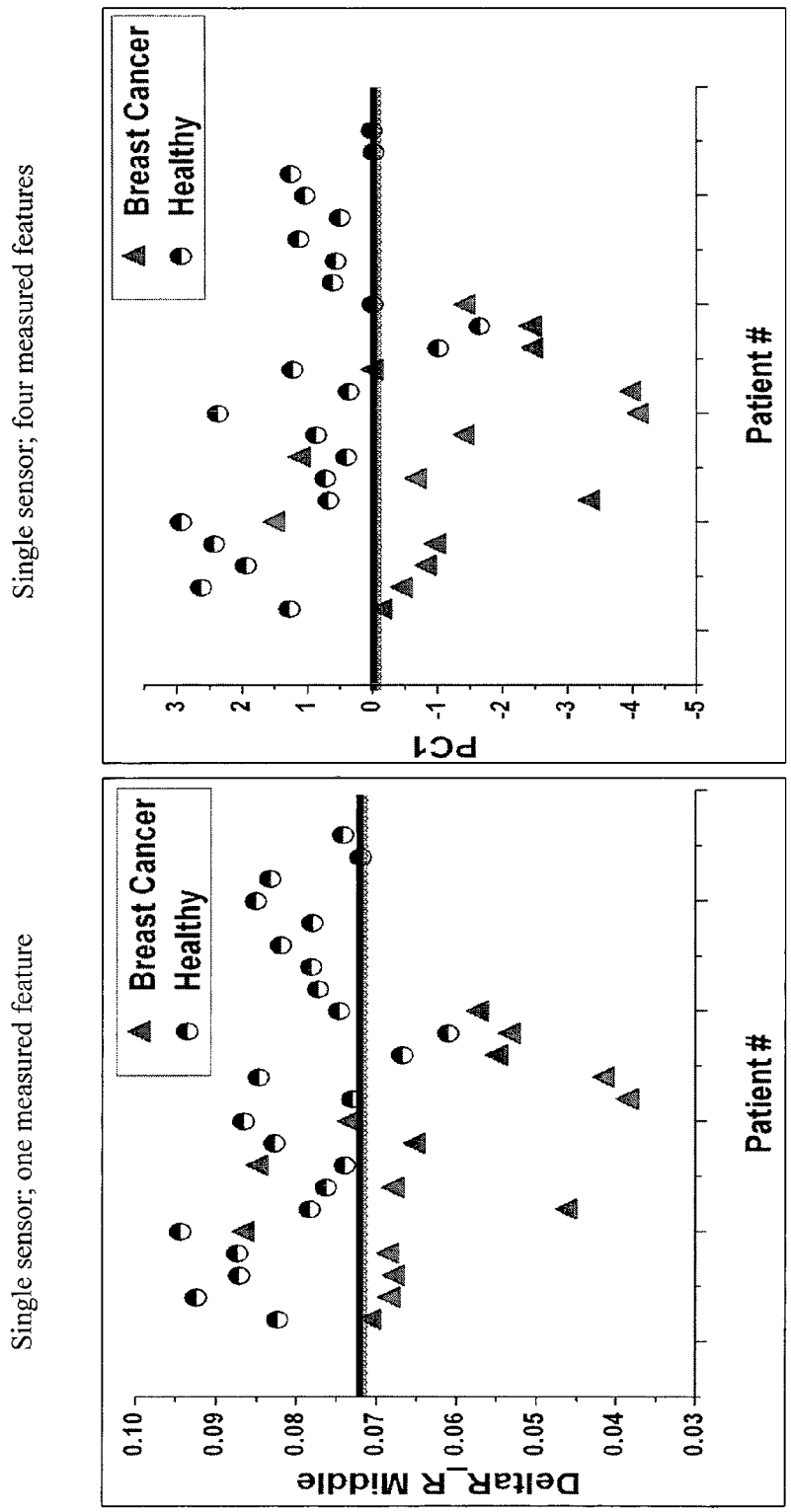
FIG. 7. Separation to healthy and BC populations based on the relative response of a single (best separating) sensor (left) compared to the separation based on 4 different measured features from the same sensor (right).

FIG. 7 shows the separation of healthy and BC populations using one sensor with a single parameter (left) and using the same sensor with four parameters (right). Whereas the use of one parameter provided five misclassifications (three breast cancer patients were erroneously classified in the healthy population and two healthy subjects were erroneously classified in the BC population), increasing the number of parameters resulted in only four misclassifications (two from each population). The separation using additional parameters was thus improved due to the reduction of noise and the supplementary data acquired from the use of additional features.

Figure 8:
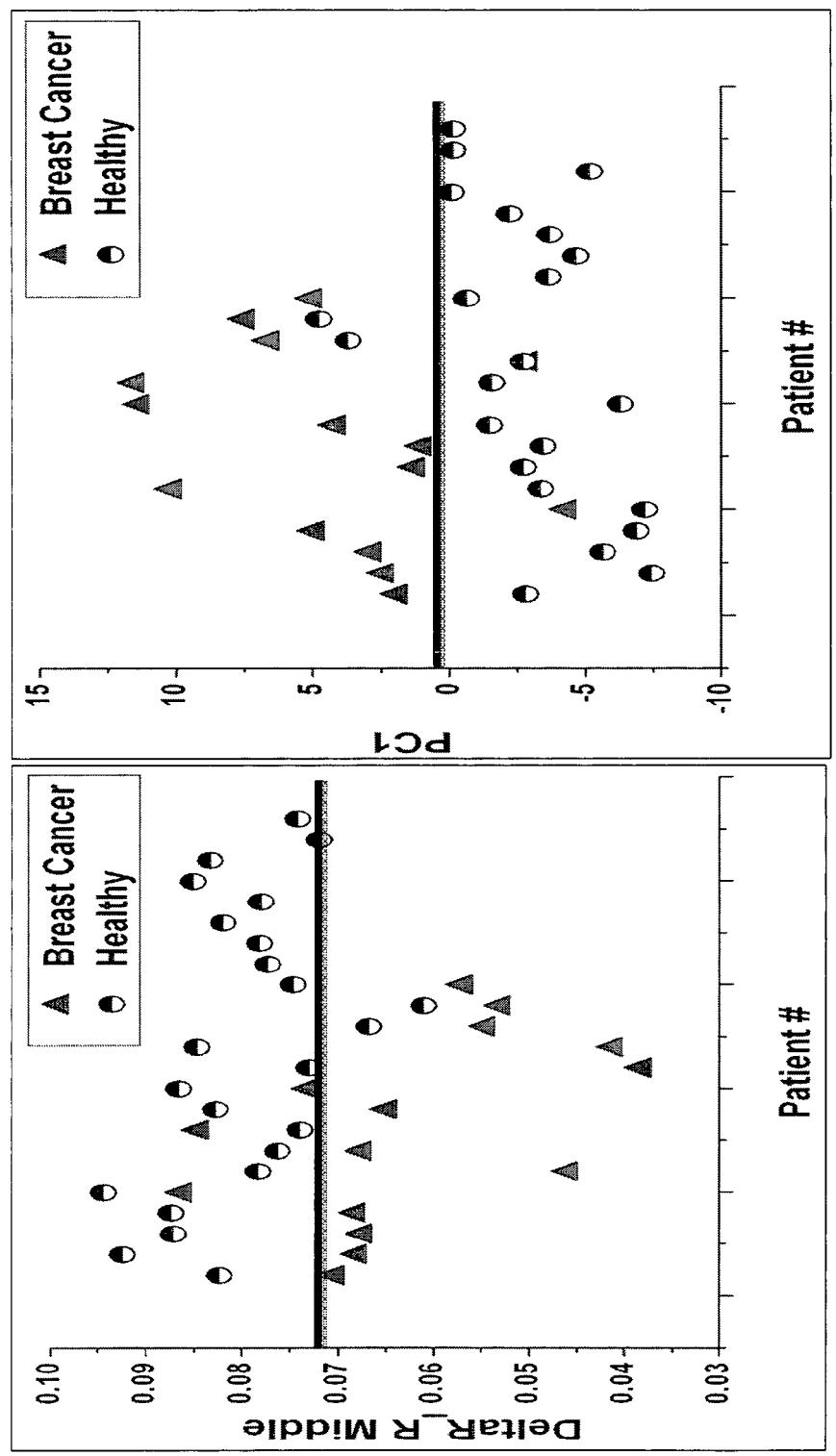
FIG. 8. Separation to healthy and BC populations based on the relative response of a single (best separating) sensor (left) compared to the separation of six sensors and 7 different measured features per each sensor (right).

FIG. 8 shows the separation of healthy and BC populations using one sensor with a single parameter (left) and using six sensors with seven parameters from each sensor (right). The combined effect of using six different sensors and measuring seven different parameters (features) per sensor reduces the number of misclassifications from five to four and further provides better separation of the two populations which is evident from the increase in the gap of the PC1 values between the two population clusters.

Hence it is clearly shown, that the additional data obtained by measuring a plurality of response induced parameters from each sensor in the sensor array provides improved separation between breath samples of healthy population and BC population and further provides improved sensitivity and specificity of the analysis. The use of multiple parameters obviates the need for additional sensors in the array.

Example 8: Collection of Breath Samples

Exhaled breath was collected in a controlled manner. The tested subjects cleared the inhaled air from ambient contaminants by repeatedly inhaling to total lung capacity for 5 min through a mouthpiece (purchased from Eco Medics) that contained a filter cartridge on the inspiratory port, thus removing more than 99.99% of exogenous VOCs from the air during inspiration. Immediately after lung washout, subjects exhaled through a separate exhalation port of the mouthpiece against 10-15 cm $H_2O$ pressure to ensure closure of the vellum and the exclusion of nasal entrainment of gas. Exhaled breath is composed of a mixture of alveolar air and respiratory dead space air. The alveolar breath can be separated from the dead space air either by collecting the breath in a $CO_2$ controlled manner or by collecting the dead space air into a separate bag prior to the collection of alveolar breath. In this experiment, subjects exhaled continuously into a breath collection kit, which enabled the automatic filling of dead space air into a separate bag and the alveolar breath into a 750 ml Mylar sampling bag (purchased from Eco Medics) in a single-step process. The Mylar bags used in this experiment were made from polyvinyl fluoride, which is chemically inert to most compounds which are present in the breath. The Mylar bags were re-used after thorough cleaning prior to each use with flowing $N_2$ (99.999% purity) gas for 5-8 minutes (GC-MS in conjugation with pre-concentration techniques showed that this purification process eliminates >99% of the contaminants and/or VOCs from the Mylar bags). Each tested subject paid 1-2 visits to the clinic within a period of 2 months or less, with a mammography routine checkup during the first visit and, if indicated, a biopsy during the second visit. Breath samples were collected during these two visits. All bags containing the breath samples were analyzed within two days from breath collection.

Example 9: Breath Analysis Using the Sensor Array

Breath samples were collected as described in Example 8 from the test population of Example 2 (table 1) with the exclusion of two subjects marked with §. All subjects were recruited from the Department of Breast Imaging, Rambam Health Care Campus (Haifa, Israel), after conventional diagnosis (as reference standard) by mammography, followed, if necessary, by biopsy, and prior to any treatment. Ethical approval was obtained from the Rambam Healthcare Campus and Technion's committee for supervision of human experiments, Haifa, Israel. The clinical trial was registered at ClinicalTrials.gov (registration no.: NCT01234987). The volunteers gave their written informed consent prior to the breath collection, and all experiments were performed according to the guidelines of the Rambam Healthcare Campus and Technion's committee for supervision of human experiments.

The samples were tested using an array of seven cross-reactive gas sensors that were based on six types of spherical gold (Au) nanoparticles (core size of 3-6 nm) with different organic coatings (tert-dodecanethiol, 2-ethylhexanethiol, 2-mercaptobenzyl alcohol, 2-mercaptobenzoazole, calixarene, or octadecylamine) and one type of cubic platinum (Pt) nanoparticles coated with benzylmercaptan. The nanoparticles were synthesized as described in detail in Dovgolevsky et al., *Small*, 4(11), 2008, 2059; and Dovgolevsky et al., *Small*, 5(10), 2009, 1158; the content of each of which is hereby incorporated in its entirety. Each sensor showed a characteristic response to all (or to a certain subset) of the VOCs found in the exhaled breath samples. The sensors were mounted into a custom poly tetrafluoroethylene circuit board inside a stainless steel test chamber with a volume of approximately 500 $cm^3$. The sampling system delivered sequence pulses of breath and vacuum to the sensors. The signal was detected by measuring a change in the electrical resistance upon exposure to VOC(s). The change was fully reversible. An Agilent Multifunction switch 34980 was used to select the active sensor and measure the responses of all sensor array elements. The entire system was computer controlled. In a typical experiment, signals of the sensor array elements were collected for 5 min in vacuum, followed by 5 min of breath samples that filled the chamber housing the array, then followed by another 5 min of vacuum. These cycles were typically repeated 2 times to test reproducibility.

Example 10: Statistical Analysis

The signals obtained as described in Example 9 were analyzed using two different approaches. In the first approach, six sensors (five sensors of spherical Au nanoparticles coated with tert-dodecanethiol, 2-ethylhexanethiol, 2-mercaptobenzyl alcohol, 2-mercaptobenzoazole, and calixarene, and one sensor of cubic Pt nanoparticles coated with benzylmercaptan) that showed statistically significant differences between (pre) malignant breast lesions and healthy states were used. Seven response induced parameters (features) were measured and analyzed from each sensor using standard PCA. The seven response induced parameters used were: $\Delta R$ start (full response at the beginning of the signal), $\Delta R/R$ start (response normalized to baseline at the beginning of the signal), $\Delta R$ middle (full response at the middle of the signal), $\Delta R/R$ middle (response normalized to baseline at middle of the signal), $\Delta R$ end (full response at the end of the signal), $\Delta R/R$ end (response normalized to baseline at the end of the signal), and rate of signal drop. The first six response induced parameters are partially dependent, and each additional feature contributes a very small amount of new information. The seventh response induced parameter (rate of signal drop) was relatively independent of the other six features. The PCA of the response induced parameters provided a visual two-dimensional presentation of breast cancer related variability in the multidimensional data. Objective cluster identification was achieved by studying the statistical distribution of the first principal component (containing more than 65% of the variance of the data) with one-way ANOVA. Separation between the test groups was analyzed using the Student's t-test.

In an independent, complimentary approach, support vector machine (SVM) analysis was used to classify the experimental data, using a total of 4 response induced parameters (features) from the sensor signal output, based on the response values at the beginning and end of the signal, along with the rate of change in those areas as follows: response start peak value, response start peak change rate, response end summation, and response end change rate summation. The SVM classification was based on two sensors, namely Au spherical nanoparticles capped with octadecylamine and Pt cubic nanoparticles capped with benzylmercaptan, using two response induced parameters per sensor. These were chosen by the SVM algorithm to give the best separation between the analyzed groups. Cross validation was utilized to evaluate the specificity and sensitivity (Cortes et al., *Machine Learning*, 30(3), 1995, 273; and Hall et al., *SIGKDD Explorations*, 11(1), 2009, 10). The subpopulations were compared by building a multi-class classifier based on a linear nu-SVC SVM classifier. Cross validation was utilized to evaluate the specificity and sensitivity by randomly dividing each sub-population into two sets, which were then used as a training set and a test set. All possible combinations of division into two sets were tested and the results were averaged. The results were stable against changing the number of folds in the cross validation.

Figure 9A:
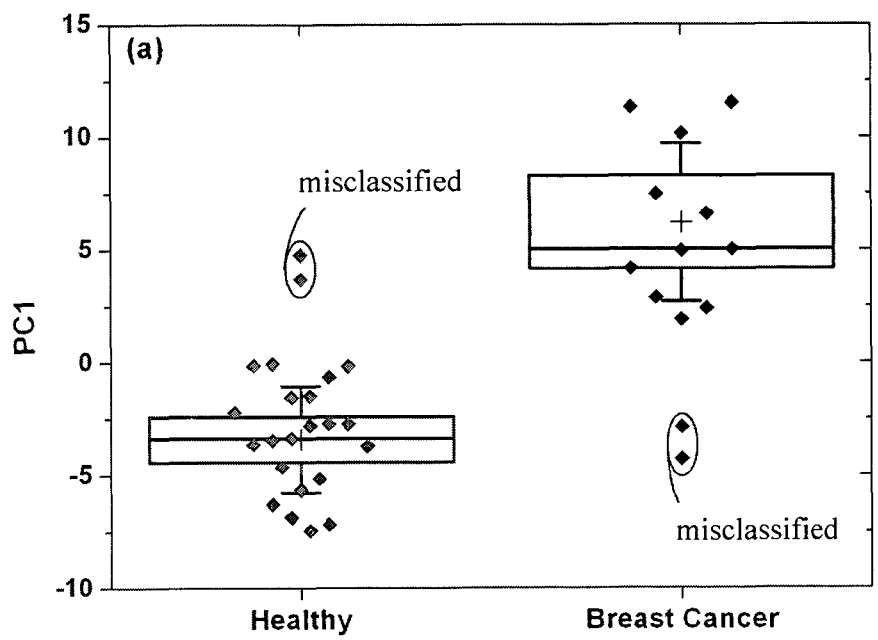
FIGS. 9A-9B. Graphical representation of the PC1 values from six sensors and 7 different measured features per each sensor (9A) healthy controls and breast cancer patients; (9B) healthy sub-populations with negative mammography and with benign breast conditions, and breast cancer population including subjects with DCIS and IDC. Each point represents one patient. The positions of the PC1 mean values are marked with +, the boxes correspond to their 95% confidence limits, and the error bars to the standard deviation of PC1.

Example 11: Classification to Healthy Controls, Subjects Having a Benign Tumor and Subjects Having a Malignant Tumor FIG. 9A shows the separation in principle component space of breath samples, of healthy population (negative PC1 values) and BC population (positive PC1 values) using an array of six sensors (five sensors of Au spherical nanoparticles each of which is capped with tert-dodecanethiol, 2-ethylhexanethiol, 2-mercaptobenzyl alcohol, 2-mercaptobenzoazole, or calixarene, and one sensor of Pt cubic nanoparticles capped with benzylmercaptan) with seven response induced parameters per each sensor. The first principle component (PC1) contained more than 65% of the variability of the data. Each point in the graph represents one test subject. Two patients were misclassified in each group. One of the misclassified cancer patients was diagnosed with tubular carcinoma, which is a well-differentiated variant of IDC with an exceptionally favorable prognosis. Without being bound by any theory or mechanism of action, the tubular carcinoma cells have a weak VOC signature, due to their resemblance to the healthy ductal cells. The mammography of the two healthy subjects that were misclassified as BC patients showed micro-calcifications (see table 1), which are associated with extra cell activity in the breast tissue. The extra cell growth is usually benign, but sometimes tight clusters of micro-calcifications can indicate very early breast cancer. Without being bound by any theory or mechanism of action, the observed micro-calcifications might possibly stem from early stage, high grade (i.e. fast developing) breast cancer that releases relatively large quantities of BC marker VOCs while the tumor is still too small to be observed.

The statistical distribution of the PC1 values was studied using ANOVA and Student's t-test as described in Example 10. Note that the Student's t-test is based on normal distribution of the data points and equal variances within the two groups that are compared. Thus, the four misclassified samples described above were not considered in this analysis. The PC1 values of the healthy and breast cancer test groups were distributed around −3.43 and 6.22, respectively (FIG. 9A and table 7a). The error bars in FIG. 9A represent the standard deviations (containing 68% of the PC1 values assuming normal distribution) and the boxes represent the 95% confidence intervals (CIs) of the PC1 mean values. Of note is that the CIs are relatively large, as a result of the small test population. Nevertheless, the boxes do not overlap and are well separated (p<0.0001). Thus, PCA analysis provides the statistically significant separation between healthy subjects (including subjects with benign tumors) and subjects having breast cancer using only one principle component. This is afforded by the use of the six tailored sensors of the present invention and a plurality (seven) of response induced parameters from each sensor.

Figure 9B:
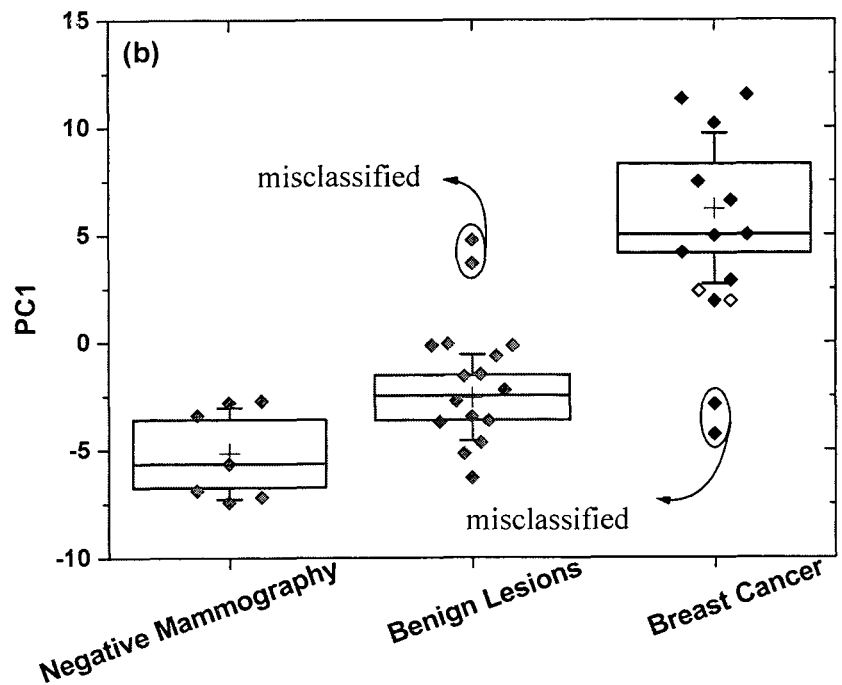

A more refined classification according to sub-populations of healthy controls (subjects with clear mammography), subjects having a benign tumor and subjects having a malignant tumor was performed. FIG. 9B and table 7b show the differences between the PC1 values corresponding to the three sub-populations. ANOVA and Student's t test yielded statistically significant differences (i) between benign breast conditions and negative mammography which were previously included in the healthy test group (p=0.04) and (ii) between benign breast conditions and malignant lesions (p<0.0001) (Table 8). The relatively large 95% CIs of the two sub-populations of subjects with clear mammography and subjects having a benign tumor overlap only marginally, as can be seen in FIG. 9B. It is contemplated that a larger clinical trial would result in smaller CIs thus improving the separation between the two sub-populations. Of note is that a separation between the two sub-populations was also observed in the signal from each of the constituent sensors. Using the sensor array of the present invention and a plurality of response induced parameters in conjunction with PCA analysis provides improved signal-to-noise ratios of the sensing signal, and, hence, increases the separation between closely related sub-populations.

TABLE 7

One-way ANOVA analysis of the PC1 values for the correctly classified subjects: Mean value of PC1, standard deviation (SD), as well as upper and lower 95% confidence limit (CL) for (a) healthy controls and cancer patients, and (b) healthy sub-populations with clear mammography or benign breast conditions and breast cancer patients with malignant lesion.

|  | Sub-population | No. of subjects | Mean PC1 | SD | Lower 95% CL | Upper 95% CL |
|---|---|---|---|---|---|---|
| (a) | BC | 11[a] | 6.22 | 3.51 | 3.86 | 8.585 |
|  | Healthy | 21[b] | −3.43 | 2.35 | −4.50 | −2.365 |
| (b) | Malignant Lesion | 11[a] | 6.22 | 3.51 | 4.59 | 7.85 |
|  | Benign Breast Conditions | 14[b] | −2.56 | 2.01 | −4.01 | −1.12 |
|  | Clear Mammography | 7 | −5.15 | 2.13 | −7.20 | −3.11 |

[a,b] Of note is that two clearly misclassified patients with malignant lesions and begin breast conditions, respectively, were excluded from the ANOVA analysis (FIG. 9A).

TABLE 8

Student's t-test for detecting statistically significant differences (a) between healthy controls and breast cancer patients, and (b) between each pair of the four sub-populations: healthy controls with clear mammography, healthy controls with benign breast conditions, and breast cancer patients.

| Sub-population 1 | Sub-population 2 | Difference of the PC1 mean values | Lower 95% CL Difference | Upper 95% CL Difference | p-value |
|---|---|---|---|---|---|
| (a) Healthy | BC | 9.64 | 12.15 | 7.13 | <0.0001 |
| (b) Negative mammography | Benign Breast Conditions | 2.59 | 0.08 | 5.09 | 0.04 |
| Benign Breast Condition | Malignant Lesion | 8.78 | 6.60 | 10.96 | <0.0001 |
| Negative mammography | Malignant Lesion | 11.37 | 8.75 | 13.98 | <0.0001 |

In a complimentary approach, SVM analysis was performed to determine the best separating line between the three sub-populations by applying a multi-class classifier to the entire experimental data using 4 response induced parameters (features) from the sensor signal output. The specificity and sensitivity was determined through cross validation as described in Example 10. The numbers of correct and incorrect patient classifications are listed in table 9. Benign breast conditions classified as such are true positive (TP), benign breast conditions classified either as clear mammography or as malignant lesions are false negative (FN). Malignant lesions and clear mammography classified as either are true negative (TN) and malignant lesions and clear mammography classified as benign breast conditions are false positive (FP). The analysis provided 94% sensitivity and 80% specificity for detecting benign breast conditions through breath testing using the sensor signal. To validate the results, label shuffling was repeatedly applied to the samples, and the SVM algorithm was ran in the same manner as in the true-labels case. The mean classification accuracy in the shuffled populations was much lower than in the true-label population, and was close to random (showing no classification ability). The shuffling test validates that the presented classification is stable and not related to noise.

TABLE 9

Number of correct and incorrect patient classifications using supportive vector machine (SVM) and cross validation.

| Negative Mammography | Benign Breast Conditions | Malignant lesions | Classified as |
|---|---|---|---|
| 5 | 2 | 0 | Negative Mammography |
| 0 | 15 | 1 | Benign Breast Conditions |
| 0 | 2 | 11 | Malignant lesions |

It is therefore demonstrated that the additional data obtained by measuring a plurality of response induced parameters provides improved separation not only between healthy and BC populations but also between more closely related sub-populations.

It is appreciated by persons skilled in the art that the present invention is not limited by what has been particularly shown and described hereinabove. Rather the scope of the present invention includes both combinations and sub-combinations of various features described hereinabove as well as variations and modifications. Therefore, the invention is not to be constructed as restricted to the particularly described embodiments, and the scope and concept of the invention will be more readily understood by references to the claims, which follow.

The invention claimed is:

1. A method of diagnosing, monitoring or prognosing cancer or identifying a benign or malignant tumor in a subject, the method comprising the steps of:
(a) providing a system comprising
(i) a sensor array comprising five sensors, wherein each sensor comprises Au nanoparticles capped with an organic coating selected from the group consisting of tert-dodecanethiol, 2-ethylhexanethiol, 2-mercaptobenzyl alcohol, 2-mercaptobenzoazole and calixarene; and one sensor comprising Pt nanoparticles capped with benzylmercaptan, and
(ii) a learning and pattern recognition analyzer wherein the learning and pattern recognition analyzer receives sensor signal outputs and compares them to stored data;
(b) exposing the sensor array to a test sample selected from exhaled breath and at least one bodily fluid or secretion of the subject;
(c) measuring a response of at least one of said sensors upon exposure to the test sample, wherein the measured response comprises a change in resistance or conductivity of the sensor upon exposure to the sample, processing the signal and extracting a plurality of response induced parameters from the measured response of the at least one sensor, wherein said response induced parameters are selected from the group consisting of full non steady state response at the beginning of the signal, full non steady state response at the beginning of the signal normalized to baseline, full non steady state response at the middle of the signal, full non steady state response at the middle of the signal normalized to baseline, full steady state response, full steady state response normalized to baseline, area under non steady state response, area under steady state response, the gradient of the response upon exposure to the test sample, the gradient of the response upon removal of the test sample, the time required to reach a certain percentage of the response upon exposure to the test sample, and the time required to reach a certain percentage of the response upon removal of the test sample; and
(d) using a learning and pattern recognition algorithm to analyze the plurality of response induced parameters extracted from the measured response and comparing them to a stored data control compiled from a set of control samples, whereby statistically significant difference between the response induced parameters of the test sample and the control, evaluated by the learning and pattern recognition algorithm or by a statistical significance test, is indicative of cancer or a malignant or benign tumor.

2. The method according to claim 1 further comprising differentiating between healthy subjects, subjects having a malignant tumor, and subjects having a benign tumor.

3. The method according to claim 1, wherein the cancer or tumor is selected from breast, brain, ovarian, colon, prostate, kidney, bladder, oral, and skin cancer or tumor.

4. The method according to claim 1, wherein the cancer or tumor is breast cancer or a benign or malignant breast tumor.

5. The method according to claim 1, wherein the organic coating comprises a monolayer or multilayers.

6. The method according to claim 1, wherein the nanoparticles capped with an organic coating are in a configuration selected from 1D wires, 2D films, and 3D assemblies.

7. The method according to claim 1, wherein the at least one sensor is used in a configuration selected from the group consisting of a chemiresistor, a chemicapacitor, a Field Effect Transistor (FET), and combinations thereof.

8. The method according to claim 1, wherein the learning and pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

9. The method according to claim 8, wherein the at least one algorithm is principal component analysis (PCA).

10. The method according to claim 1, comprising extracting at least four response induced parameters from the measured response.

11. The method according to claim 10, wherein the at least four response induced parameters comprise full non-steady state response at the beginning of the signal, full non-steady state response at the beginning of the signal normalized to baseline, full non-steady state response at the middle of the signal, and the gradient of response upon removal of the test sample.

12. The method according to claim 1, wherein the certain percentage of the response is selected from the group consisting of 10%, 20%, 30%, 40%, 50%, 60%, 70%, 80%, 90% and 100%.

13. The method according to claim 1, wherein the at least one bodily fluid or secretion is selected from the group consisting of serum, urine, feces, sweat, vaginal discharge, saliva and sperm.

14. The method according to claim 1, wherein the set of control samples comprises control samples selected from the group consisting of samples obtained from healthy subjects, samples obtained from subjects having a benign tumor, samples obtained from subjects having a malignant tumor, and combinations thereof.

15. The method according to claim 14, for diagnosing or prognosing cancer or identifying a malignant tumor in a subject, wherein the set of control samples comprises samples obtained from healthy subjects and/or samples obtained from subjects having a benign tumor, and wherein the statistically significant difference between the response induced parameters of the test sample and the control is indicative of cancer or a malignant tumor.

16. The method according to claim 14, for identifying a benign tumor in a subject, wherein the set of control samples comprises samples obtained from healthy subjects and/or samples obtained from subjects having a malignant tumor, and wherein the statistically significant difference between the response induced parameters of the test sample and the control is indicative of a benign tumor.

17. A method of diagnosing, monitoring or prognosing cancer or identifying a benign or malignant tumor in a subject, the method comprising the steps of:
 (a) providing a system comprising
  (i) at least one sensor comprising a sensor array comprising five sensors, wherein each sensor comprises Au nanoparticles capped with an organic coating selected from the group consisting of tert-dodecanethiol, 2-ethylhexanethiol, 2-mercaptobenzyl alcohol, 2-mercaptobenzoazole and calixarene; and one sensor comprising Pt nanoparticles capped with benzylmercaptan, and
  (ii) a learning and pattern recognition analyzer wherein the learning and pattern recognition analyzer receives sensor signal outputs and compares them to stored data;
 (b) exposing the sensor array to a test sample selected from exhaled breath and at least one bodily fluid or secretion of the subject;
 (c) measuring a response of at least one of said sensors upon exposure to the test sample, wherein the measured response comprises a change in any one or more of an electrical property selected from resistance, impedance, capacitance, inductance, conductivity, and optical properties of the sensor upon exposure to the sample, processing the signal and extracting at least four response induced parameters from the measured response of the at least one sensor; and
 (d) using a learning and pattern recognition algorithm to analyze the at least four response induced parameters extracted from the measured response of the at least one sensor, and comparing them to a stored data control compiled from a set of control samples, whereby statistically significant difference between the response induced parameters of the test sample and the control, evaluated by the learning and pattern recognition algorithm or by a statistical significance test, is indicative of cancer or a malignant or benign tumor.

18. The method of according to claim 17, wherein the at least four response induced parameters are selected from the group consisting of full non steady state response at the beginning of the signal, full non steady state response at the beginning of the signal normalized to baseline, full non steady state response at the middle of the signal, full non steady state response at the middle of the signal normalized to baseline, full steady state response, full steady state response normalized to baseline, area under non steady state response, area under steady state response, the gradient of the response upon exposure to the test sample, the gradient of the response upon removal of the test sample, the time required to reach a certain percentage of the response upon exposure to the test sample, and the time required to reach a certain percentage of the response upon removal of the test sample.

* * * * *